US012648790B2

(12) United States Patent
Fischer et al.

(10) Patent No.: US 12,648,790 B2
(45) Date of Patent: Jun. 9, 2026

(54) FLEXIBLE DRIVE MEMBER ATTACHMENT THROUGH ADDITIVE THERMAL SPRAY

(71) Applicant: CILAG GMBH INTERNATIONAL, Zug (CH)

(72) Inventors: Austin Michael Fischer, Cincinnati, OH (US); Guowei John Zhang, Cincinnati, OH (US); Steve Smolik, Cincinnati, OH (US); Jeff Clark, Blue Ash, OH (US)

(73) Assignee: Cilag GmbH International, Zug (CH)

( * ) Notice: Subject to any disclaimer, the term of this patent is extended or adjusted under 35 U.S.C. 154(b) by 2 days.

(21) Appl. No.: 18/767,606

(22) Filed: Jul. 9, 2024

(65) Prior Publication Data

US 2026/0013899 A1 Jan. 15, 2026

(51) Int. Cl.
A61B 17/3211 (2006.01)
A61B 17/00 (2006.01)

(52) U.S. Cl.
CPC . A61B 17/3211 (2013.01); *A61B 2017/00526* (2013.01); *A61B 2017/00867* (2013.01)

(58) Field of Classification Search
CPC ...... A61B 17/3211; A61B 2017/00526; A61B 2017/00867
See application file for complete search history.

(56) References Cited

U.S. PATENT DOCUMENTS

2009/0012520 A1 1/2009 Hixson et al.
2015/0066076 A1 3/2015 Kerr et al.

2017/0296258 A1 10/2017 Bucciaglia et al.
2020/0129198 A1* 4/2020 Davison ................. A61B 34/71
2020/0178994 A1 6/2020 Honegger
2023/0053807 A1 2/2023 Brause
2023/0055798 A1* 2/2023 Brause ............... A61B 17/3211
2023/0135824 A1 5/2023 Johnson et al.

FOREIGN PATENT DOCUMENTS

WO 2023073524 A2 5/2023

OTHER PUBLICATIONS

The International Search Report for PCT/IB2025/056952, mailed Dec. 2, 2025, 24 pages.
Invitation to Pay Additional Fees received in PCT Application No. PCT/IB2025/056952, mailed on Oct. 7, 2025, 11 pages.

* cited by examiner

*Primary Examiner* — Anh T Dang
(74) *Attorney, Agent, or Firm* — Vorys, Sater, Seymour and Pease LLP

(57) ABSTRACT

A surgical tool includes a drive housing having a drive input mounted thereon and a shaft extending distally from the drive housing that terminates at an end effector. A knife assembly of the surgical tool includes a blade member defining a cutting edge at a distal end thereof and disposed within the end effector. The blade member is constructed of a first material such a stainless-steel. The knife assembly also includes a drive rod extending through the shaft and having a proximal end operably coupled to the drive input to translate the drive rod longitudinally through the shaft and the blade member through the end effector in response to actuation of the drive input. The drive rod further includes a distal portion constructed of a second material dissimilar to the first material, and the distal portion of the drive rod is coupled directly to the blade member.

20 Claims, 16 Drawing Sheets

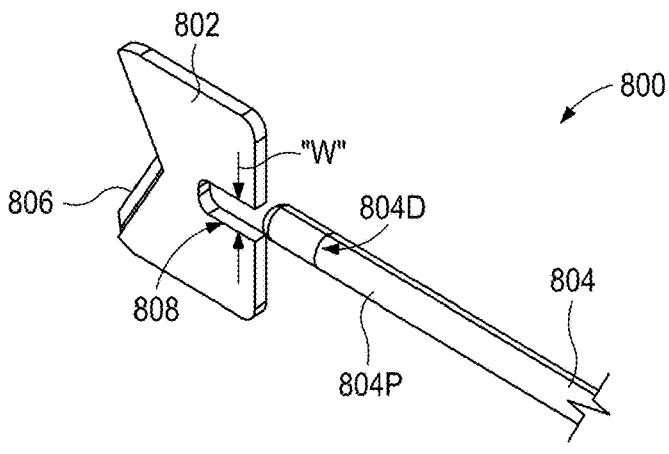
FIG. 8A
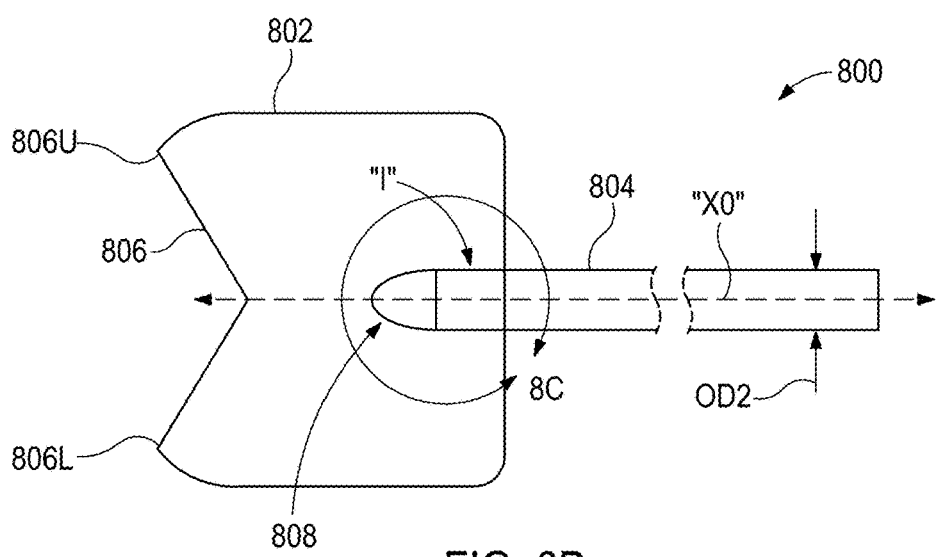
FIG. 8B
FIG. 8C

FLEXIBLE DRIVE MEMBER ATTACHMENT THROUGH ADDITIVE THERMAL SPRAY

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

Some instruments include a cutting instrument or "knife" operable to traverse a blade member through a guide track in the end effector to sever tissue. The blade member is often driven along the guide track by a drive rod extending through the wrist. The drive rod must be sufficiently rigid to advance the blade member through tissue, while being sufficiently flexible to permit the end effector to be articulated at the wrist. Specialty metals, such as nitinol, may be suitable for the construction of drive rods because these specialty metals may provide the appropriate rigidity and flexibility characteristics. These specialty metals, however, may not be readily joined with materials common in the construction of the blade member itself, such as stainless steel.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 8A, 8B and 8C are respectively an exploded perspective view, a side view and a detail view of a knife assembly with a blade member secured directly to a distal portion of a drive rod in accordance with one or more embodiments consistent with the present disclosure.

DETAILED DESCRIPTION

The present disclosure is related to robotic surgical systems and, more particularly, to knife assemblies for surgical tools having a direct connection between a blade member and a distal portion of a drive rod constructed of dissimilar materials. As used herein, a "direct connection" includes a permanent joint defined at an intersection wherein the blade member and a distal portion of a drive rod engage one another.

Embodiments discussed herein describe a surgical tool that includes a drive housing having a drive input rotatably mounted thereon and a shaft extending distally from the drive housing and terminating at an end effector. A knife assembly of the surgical tool includes a blade member defining a cutting edge at a distal end thereof and disposed within, and movable relative to, the end effector. The blade member is constructed of a first material, such as stainless-steel. The knife assembly also includes a drive rod extending through the shaft and having a proximal end operably coupled to the drive input to translate the drive rod longitudinally through the shaft and the blade member through the end effector in response to actuation of the drive input. The drive rod further includes a distal portion constructed of a second material dissimilar to the first material, such as nitinol. The distal portion of the drive rod is coupled directly to the blade member. The direct connection may be established by a thermal spray deposited over at least a portion of an intersection between the blade member and the distal portion of the drive rod. Alternatively, or additionally, the blade member and the distal portion of the drive rod may have complementarily interlocking geometry and be swaged to one another to establish or supplement the direct connection between the two components.

Embodiments discussed herein describe a surgical tool that includes a drive housing having a drive input mounted thereon and a shaft extending distally from the drive housing and terminating at an end effector. A knife assembly of the surgical tool includes a blade member defining a cutting edge at a distal end thereof and disposed within the end effector. The blade member is constructed of a first material, such a stainless steel. The knife assembly also includes a drive rod extending through the shaft and having a proximal end operably coupled to the drive input to translate the drive rod longitudinally through the shaft and the blade member through the end effector in response to actuation of the drive input. The drive rod further includes a distal portion constructed of a second material dissimilar to the first material, and the distal portion of the drive rod is coupled directly to the blade member.

Figure 1:
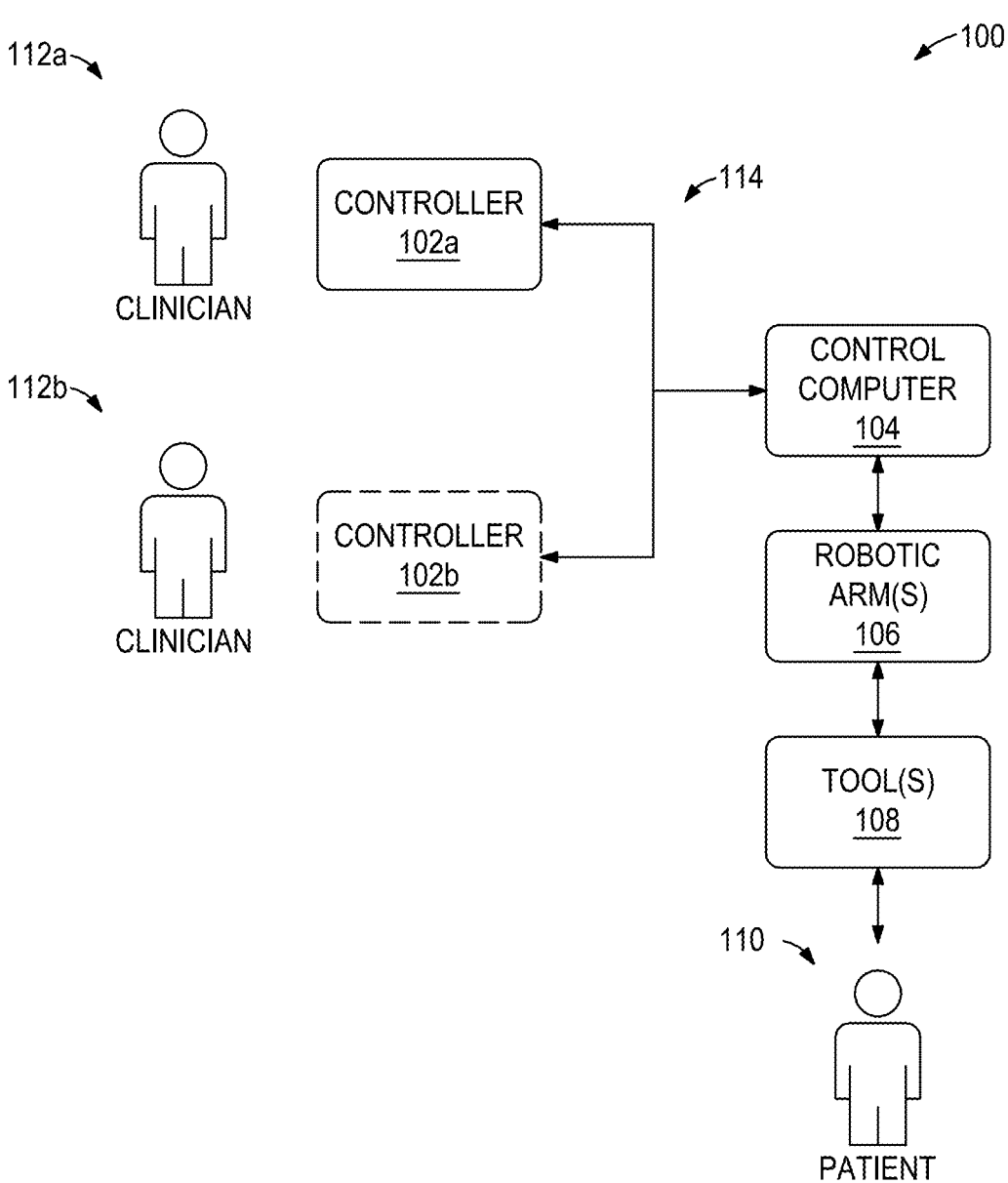
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed line) may be operated by a second clinician 112b to direct operation of the robotic arms 106 and tools 108 via the control computer 104 and in conjunction with the first clinician 112a. In such embodiments, for example, each clinician 112a,b may control different robotic arms 106 or, in some cases, complete control of the robotic arms 106 may be passed between the clinicians 112a,b as needed. In some embodiments, additional robotic manipulators having additional robotic arms may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Figures 2, 3:
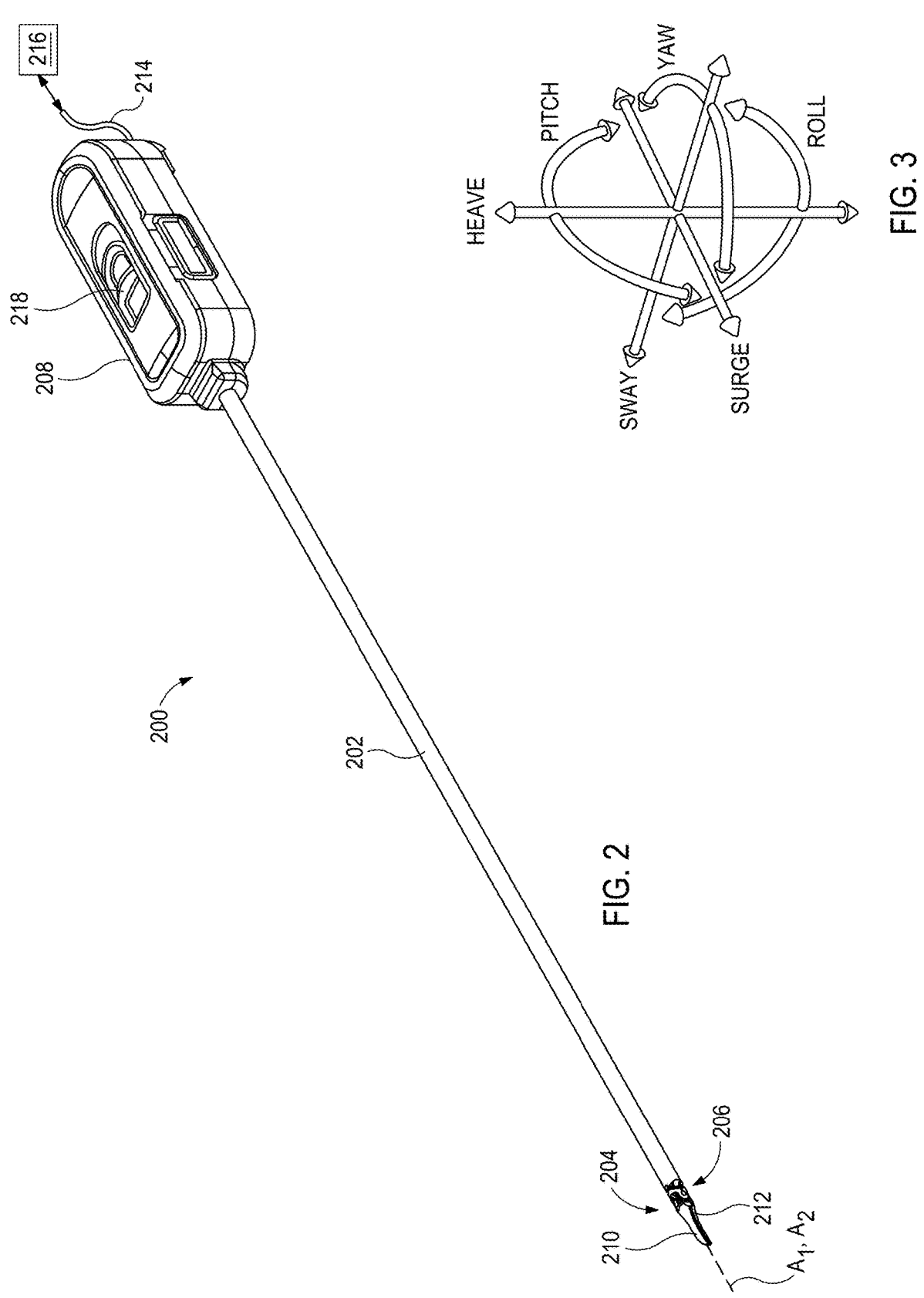
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

The surgical tool 200 may further include a manual release switch 218 that may be manually actuated by a user (e.g., a surgeon) to override the cable driven system and thereby manually articulate or operate the end effector 204. The release switch 218 is movably positioned on the drive housing 208, and a user is able to manually move (slide) the release switch 218 from a disengaged position, as shown, to an engaged position. In the disengaged position, the surgical tool 200 is able to operate as normal. As the release switch 218 moves to the engaged position, however, various internal component parts of the drive housing 208 are simultaneously moved, thereby resulting in the jaws 210, 212 opening, which might prove beneficial for a variety of reasons. In some applications, for example, the release switch 218 may be moved in the event of an electrical disruption that renders the surgical tool 200 inoperable. In such applications, the user would be able to manually open the jaws 210, 212 and thereby release any grasped tissue and remove the surgical tool 200. In other applications, the release switch 218 may be actuated (enabled) to open the jaws 210, 212 in preparation for cleaning and/or sterilization of the surgical tool 200.

Figure 4A:
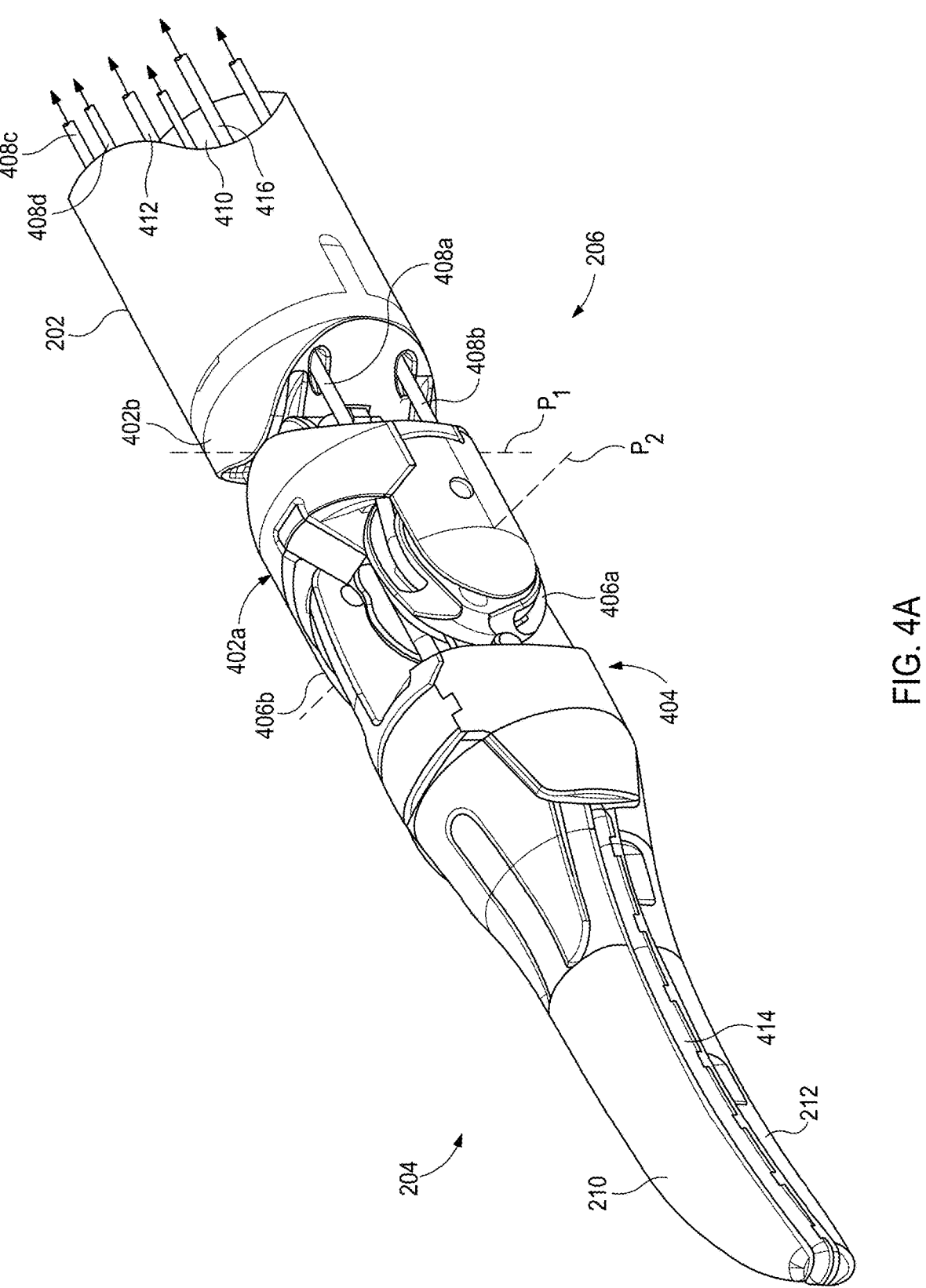
FIG. 4A is an enlarged isometric view of the distal end of the surgical tool of FIG. 2.

FIG. 4A is an enlarged isometric view of the distal end of the surgical tool 200. More specifically, FIG. 4A depicts an enlarged view of the end effector 204 and the wrist 206, with the jaws 210, 212 of the end effector 204 in the closed position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" clevis 402a and a second or "proximal" clevis 402b. The clevises 402a,b are alternatively referred to as "articulation joints" of the wrist 206 and extend from the shaft 202 (or alternatively a shaft adapter). The clevises 402a,b are operatively coupled to facilitate articulation of the wrist 206 relative to the shaft 202. As illustrated, the wrist 206 also includes a linkage 404 arranged distal to the distal clevis 402a and operatively mounted to the jaws 210, 212.

The proximal end of the distal clevis 402a may be rotatably mounted or pivotably coupled to the proximal clevis 402b at a first pivot axis $P_1$ of the wrist 206. In some embodiments, an axle may extend through the first pivot axis $P_1$ and the distal and proximal clevises 402a,b may be rotatably coupled via the axle. In other embodiments, however, such as is depicted in FIG. 4A, the distal and proximal clevises 402a,b may be engaged in rolling contact, such as via an intermeshed gear relationship that allows the clevises 402a,b to rotate relative to each other similar to a rolling joint.

First and second pulleys 406a and 406b may be rotatably mounted to the distal end of the distal clevis 402a at a second pivot axis $P_2$ of the wrist 206. The linkage 404 may be arranged distal to the second pivot axis $P_2$ and operatively mounted to the jaws 210, 212. The first pivot axis $P_1$ is substantially perpendicular (orthogonal) to the longitudinal axis $A_1$ of the shaft 202, and the second pivot axis $P_2$ is substantially perpendicular (orthogonal) to both the longitudinal axis $A_1$ and the first pivot axis $P_1$. Movement of the end effector 204 about the first pivot axis $P_1$ provides "yaw" articulation of the wrist 206, and movement about the second pivot axis $P_2$ provides "pitch" articulation of the wrist 206.

A plurality of drive cables, shown as drive cables 408a, 408b, 408c, and 408d, extend longitudinally within a lumen 410 defined by the shaft 202 (or a shaft adaptor) and extend at least partially through the wrist 206. The drive cables 408a-d may form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 408a-d can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 408a-d are depicted in FIG. 4A, more or less than four may be employed, without departing from the scope of the disclosure.

The drive cables 408a-d extend proximally from the end effector 204 and the wrist 206 toward the drive housing 208 (FIG. 2) where they are operatively coupled to various actuation mechanisms or devices that facilitate longitudinal movement (translation) of the drive cables 408a-d within the lumen 410. Selective actuation of the drive cables 408a-d applies tension (i.e., pull force) to the given drive cable 408a-d in the proximal direction, which urges the given drive cable 408a-d to translate longitudinally within the lumen 410.

In the illustrated embodiment, the drive cables 408a-d each extend longitudinally through the proximal clevis 402b. The distal end of each drive cable 408a-d terminates at the first or second pulleys 406a,b, thus operatively coupling each drive cable 408a-d to the end effector 204. In some embodiments, the distal ends of the first and second drive cables 408a,b may be coupled to each other and terminate at the first pulley 406a, and the distal ends of the third and fourth drive cables 408c,d may be coupled to each other and terminate at the second pulley 406b. In at least one embodiment, the distal ends of the first and second drive cables 408a,b and the distal ends of the third and fourth drive cables 408c,d may each be coupled together at corresponding ball crimps (not shown) mounted to the first and second pulleys 406a,b, respectively.

In at least one embodiment, the drive cables 408a-d may operate "antagonistically". More specifically, when the first drive cable 408a is actuated (moved), the second drive cable 408b naturally follows as coupled to the first drive cable 408a, and when the third drive cable 408c is actuated, the fourth drive cable 408d naturally follows as coupled to the third drive cable 408c, and vice versa. Antagonistic operation of the drive cables 408a-d can open or close the jaws 210, 212. More specifically, selective actuation of the drive cables 408a-d in other known configurations or coordination will cause the jaws 210, 212 to open or close. Antagonistic operation of the drive cables 408a-d can further cause the end effector 204 to articulate at the wrist 206. More specifically, selective actuation of the drive cables 408a-d in known configurations or coordination can cause the end effector 204 to articulate about one or both of the pivot axes $P_1$, $P_2$, thus facilitating articulation of the end effector 204 in both pitch and yaw directions, either individually or simultaneously. Antagonistic operation of the drive cables 408a-d advantageously reduces the number of cables required to provide full wrist 206 motion, and also helps eliminate slack in the drive cables 408a-d, which results in more precise motion of the end effector 204.

In the illustrated embodiment, the end effector 204 is able to articulate (move) in pitch about the second or "pitch" pivot axis $P_2$, which is located near the distal end of the wrist 206. Thus, the jaws 210, 212 open and close in the direction of pitch. In other embodiments, however, the wrist 206 may alternatively be configured such that the second pivot axis $P_2$ facilitates yaw articulation of the jaws 210, 212, without departing from the scope of the disclosure.

In some embodiments, an electrical conductor 412 may also extend longitudinally within the lumen 410, through the wrist 206, and terminate at an electrode 414 to supply electrical energy to the end effector 204. In some embodiments, the electrical conductor 412 may comprise a wire, but may alternatively comprise a rigid or semi-rigid shaft, rod, or strip (ribbon) made of a conductive material. The electrical conductor 412 may be entirely or partially covered with an insulative covering (overmold) made of a non-conductive material. Using the electrical conductor 412 and the electrode 414, the end effector 204 may be configured for monopolar or bipolar RF operation.

In the illustrated embodiment, the end effector 204 comprises a combination tissue grasper and vessel sealer that includes a blade member 420 (FIG. 4B), alternately referred to as a "cutting element" or "knife." The blade member 420 is aligned with and configured to traverse a guide track 422 (FIG. 4B) defined longitudinally in one or both of the upper and lower jaws 210, 212. The blade member 420 may be operatively coupled to the distal end of a drive rod 416 that extends longitudinally within the lumen 410 and passes through the wrist 206. Longitudinal movement (translation) of the drive rod 416 correspondingly moves the blade member 420 within the guide track(s) 422. Similar to the drive cables 408a-d, the drive rod 416 may form part of the actuation systems housed within the drive housing 208 (FIG. 2). Selective actuation of a corresponding drive input will cause the drive rod 416 to move distally or proximally within the lumen 410, and correspondingly move the blade member 420 in the same longitudinal direction.

Figure 4B:
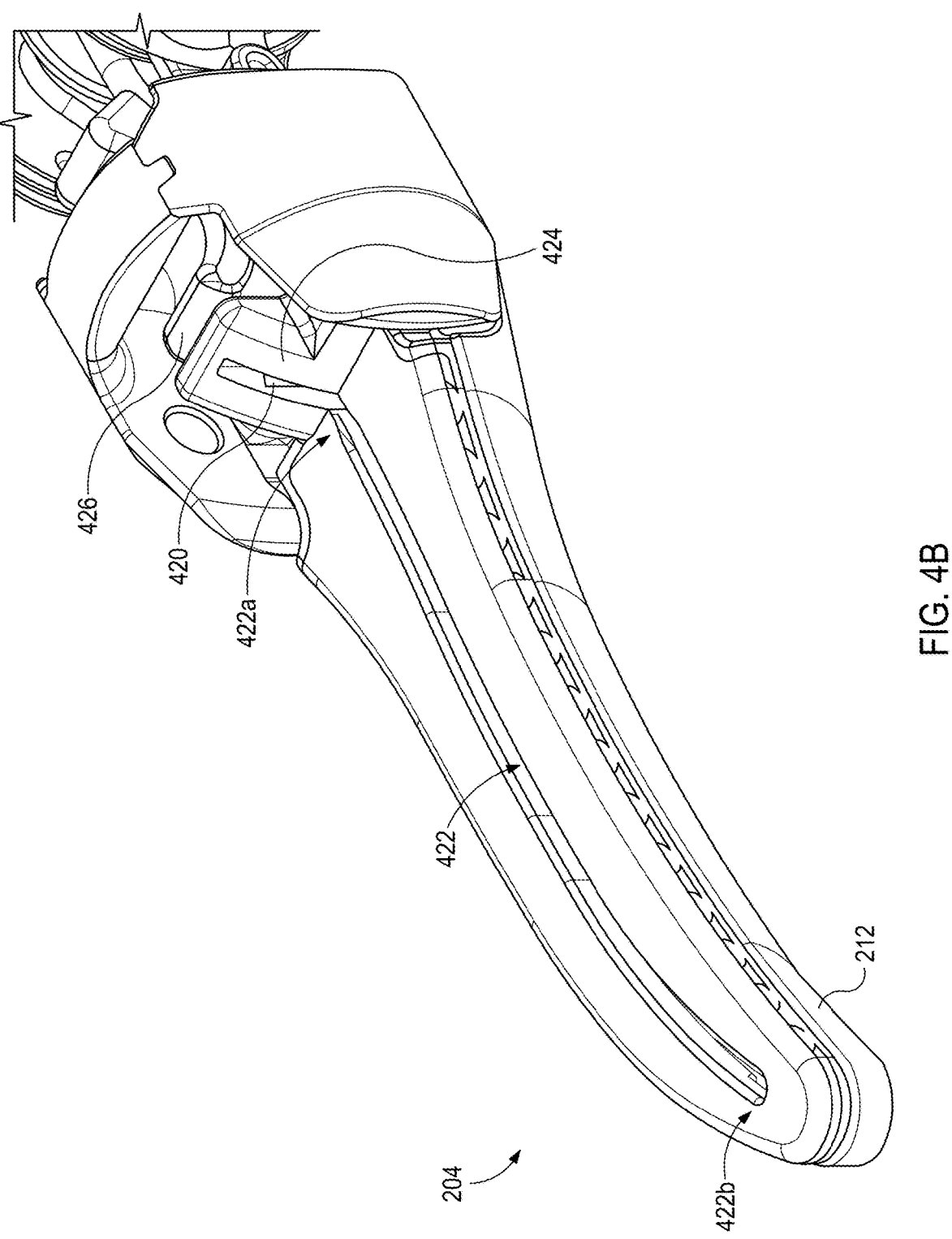
FIG. 4B is a partial isometric view of the distal end of the surgical tool of FIG. 2 with a jaw removed.

FIG. 4B is a partial isometric view of the distal end of the surgical tool 200 with the first jaw 210 (FIG. 4A) removed. With the first jaw 210 removed, the guide track 422 defined in the second jaw 212 is visible extending from a proximal end 422a to a distal end 422b. In some embodiments, the first jaw 210 may include a similar or complimentary guide track (not shown) in opposition to the guide track 422 when the first and second jaws 210, 212 are closed. The blade member 420 (partially visible) is illustrated in a "zero" or "home" position wherein the blade member 420 is disposed within a knife housing 424 adjacent the proximal end 422a of the guide track 422. The knife housing 424 may be constructed of a non-conductive material and as a separate component. When the blade member 420 is disposed within the knife housing 424, the end effector 204 may be safely handled for cleaning or maintenance. In operation, the blade member 420 may be selectively moved distally out of the knife housing 424 along the guide track 422 by longitudinally moving the drive rod 416 as described above.

A distal wedge 426 is disposed proximally of the knife housing 424. As described in greater detail below, the distal wedge 426 is a component of a distal support mechanism 1602 (FIG. 16) that supports the drive rod 416 when the blade member 420 is moved distally out of the knife housing 424, or when the drive rod 416 is otherwise under loading. At least a portion of the blade member 420 may be housed within the distal wedge 426 when the blade member 420 is in the "zero" or "home" position.

Figure 5:
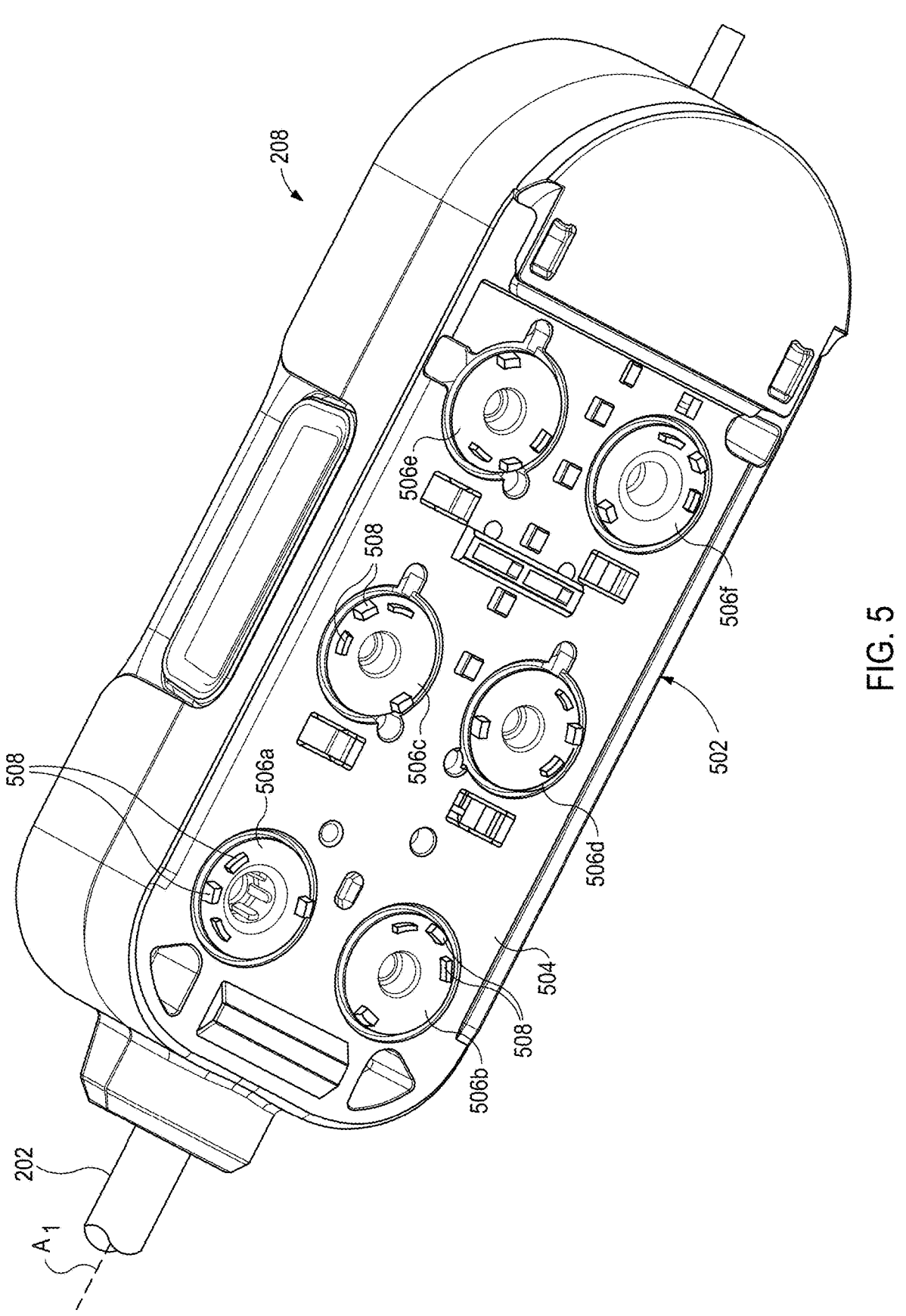
FIG. 5 is a bottom view of the drive housing of FIG. 2, according to one or more embodiments.

FIG. 5 is a bottom view of the drive housing 208, according to one or more embodiments. As illustrated, the drive housing 208 may include a tool mounting portion 502 used to operatively couple the drive housing 208 to a tool driver of a robotic manipulator. The tool mounting portion 502 may releasably couple the drive housing 208 to a tool driver in a variety of ways, such as by clamping thereto, clipping thereto, or slidably mating therewith. In some embodiments, the tool mounting portion 502 may include an array of electrical connecting pins, which may be coupled to an electrical connection on the mounting surface of the tool driver. While the tool mounting portion 502 is described herein with reference to mechanical, electrical, and magnetic coupling elements, it should be understood that a wide variety of telemetry modalities might be used, including infrared, inductive coupling, or the like.

The tool mounting portion 502 includes and otherwise provides an interface 504 configured to mechanically, magnetically, and/or electrically couple the drive housing 208 to the tool driver. As illustrated, the interface 504 includes and supports a plurality of drive inputs, shown as drive inputs 506a, 506b, 506c, 506d, 506e, and 506f. Each drive input 506a-f comprises a rotatable disc configured to align with and couple to a corresponding actuator or "drive output" of a tool driver, such that rotation (actuation) of a given drive output drives (rotates) a corresponding one of the drive inputs 506a-f. Each drive input 506a-f may provide or define one or more surface features 508 configured to align with mating surface features provided on the corresponding drive output. The surface features 508 can include, for example, various protrusions and/or indentations that facilitate a mating engagement. In some embodiments, some or all of the drive inputs 506a-f may include one surface feature 508 that is positioned closer to an axis of rotation of the associated drive input 506a-f than the other surface feature(s) 508. This may help to ensure positive angular alignment of each drive input 506a-f.

In some embodiments, actuation of the first drive input 506a may be configured to control rotation of the shaft 202 about its longitudinal axis $A_1$. The shaft 202 may be rotated clockwise or counter-clockwise depending on the rotational actuation of the first drive input 506a. In some embodiments, actuation of the second, third, fourth, and fifth drive inputs 506b-e may be configured to operate movement (axial translation) of the drive cables 408a-d (FIG. 4A), which results in the actuation of the wrist 206 (FIG. 4A) and/or articulation (operation) of the end effector 204 (FIG. 4A). In some embodiments, actuation of the sixth drive input 506*f* may be configured to advance and retract the drive rod 416 (FIG. 4A), and thereby correspondingly advance or retract the blade member 420 (FIG. 4B) at the end effector 204. Each of the drive inputs 506*a-f* may be actuated based on user inputs communicated to the tool driver coupled to the interface 504, and the user inputs may be received via a computer system incorporated into the robotic surgical system.

Figure 6:
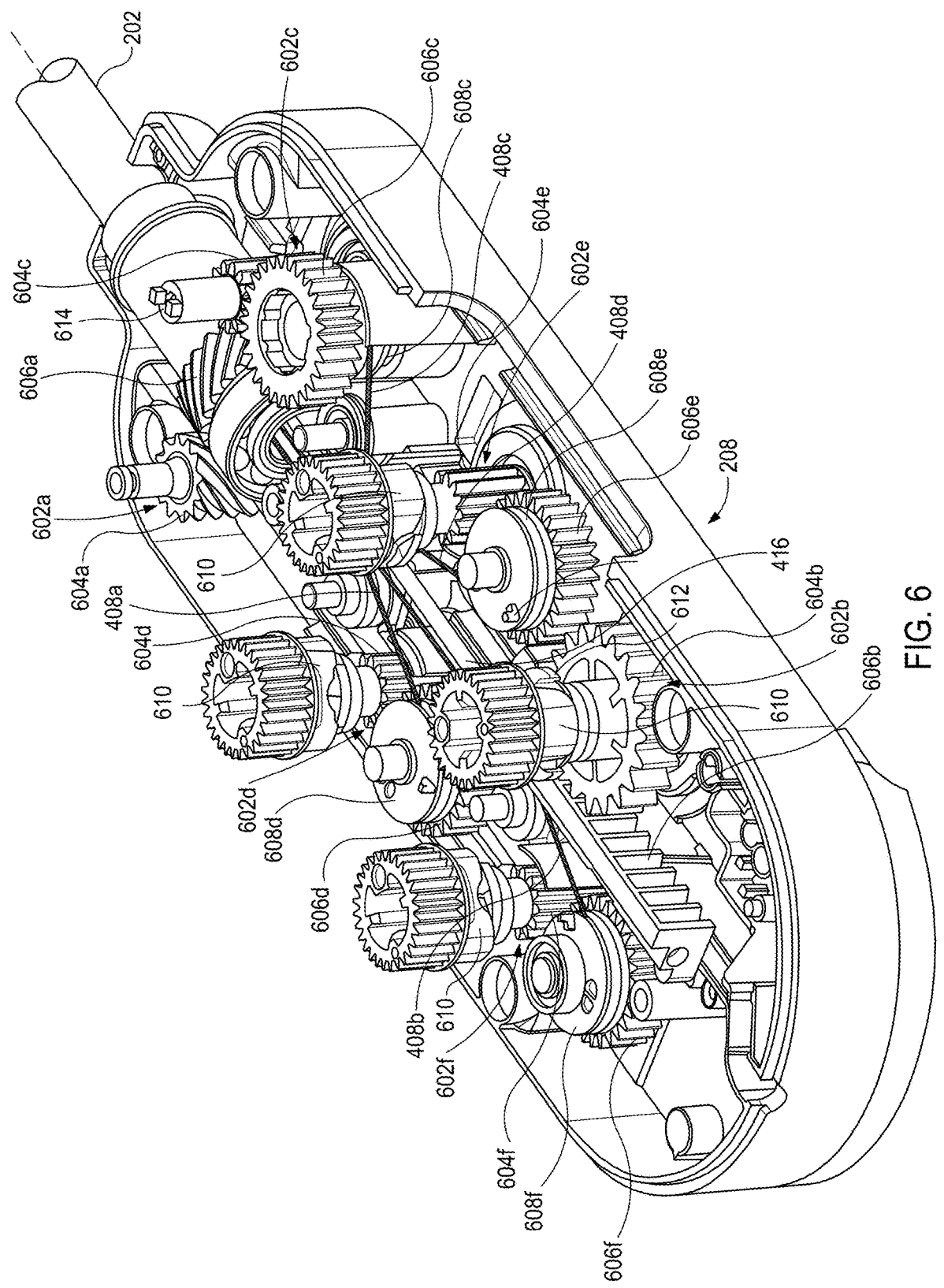
FIG. 6 is an exposed isometric view of the interior of the drive housing of FIG. 2, partially illustrating a plurality of capstan assemblies for driving a knife and other functions of the surgical tool, according to one or more embodiments.

FIG. 6 is an exposed isometric view of the interior of the drive housing 208, according to one or more embodiments. Several component parts that may be otherwise contained within the drive housing 208 are not shown in FIG. 6 to enable discussion of the depicted component parts. As illustrated, the drive housing 208 houses and otherwise contains a plurality of capstan assemblies operable to operate surgical tool 200 (FIG. 2). In particular, a first capstan assembly 602*a* is contained (housed) within the drive housing 208. As illustrated, the first capstan assembly 602*a* may include a drive gear 604*a*, which may be operatively coupled to or extend from the first drive input 506*a* (FIG. 5) such that actuation of the first drive input 506*a* results in rotation of the drive gear 604*a*. In the illustrated embodiment, the drive gear 604*a* comprises a worm gear, e.g., a crossed helical or screw gear, which may be configured to mesh and interact with a driven gear 606*a* secured within the drive housing 208 and operatively coupled to the shaft 202 such that rotation of the driven gear 606*a* correspondingly rotates the shaft 202. Accordingly, actuation of the first capstan assembly 602*a*, via actuation of the first drive input 506*a*, will drive the driven gear 606*a* and thereby control rotation of the elongate shaft 202 about the longitudinal axis A₁.

The drive housing 208 may further contain or house a second capstan assembly 602*b*, which may include a drive gear 604*b* operatively coupled to or extending from the sixth drive input 506*f* (FIG. 5) such that actuation of the sixth drive input 506*f* results in rotation of the drive gear 604*b*. The drive gear 604*b* is a rotary pinion gear arranged to intermesh with a longitudinally driven gear 606*b* positioned within the drive housing 208. In the illustrated embodiment, the driven gear 606*b* comprises a rack gear longitudinally translatable within the drive housing 208 as acted upon by the drive gear 604*b*. The drive rod 416 may be operatively coupled to the driven gear 606*b* and extend distally therefrom to the end effector 204 (FIGS. 2 and 4). Accordingly, actuation of the second capstan assembly 602*b*, via actuation of the sixth drive input 506*f*, will cause the driven gear 606*b* to longitudinally translate and correspondingly advance or retract the drive rod 416 and the blade member 420 (FIG. 4B) coupled to the end of the drive rod 416 at the end effector 204.

The drive housing 208 further contains or houses third, fourth, fifth, and sixth capstan assemblies 602*c*, 602*d*, 602*e*, and 602*f*, alternately be referred to as "drive cable" capstan assemblies since they are operable to actuate the drive cables 408*a-d*, as described below. While four "drive cable" capstan assemblies 602*c-f* are depicted in FIG. 6, alternative embodiments may include more or less than four, depending on how many drive cables 408*a-d* are used.

In the illustrated embodiment, the third capstan assembly 602*c* is actuated through operation (rotation) of the second drive input 506*b* (FIG. 5), the fourth capstan assembly 602*d* is actuated through operation (rotation) of the third drive input 506*c* (FIG. 5), the fifth capstan assembly 602*e* is actuated through operation (rotation) of the fourth drive input 506*d* (FIG. 5), and the sixth capstan assembly 602*f* is actuated through operation (rotation) of the fifth drive input 506*e* (FIG. 5). As illustrated, each capstan assembly 602*c-f* includes a drive gear 604*c*, 604*d*, 604*e*, and 604*f* that is coupled to or extends from the corresponding drive input 506*b-e*, respectively, such that actuation (rotation) of the drive input 506*b-e* correspondingly rotates the associated drive gear 604*c-f*, respectively.

Moreover, each drive gear 604*c-f* is positioned to mesh and interact with a corresponding driven gear 606*c*, 606*d*, 606*e*, and 606*f* rotatably mounted within the drive housing 208. Each driven gear 606*c-f* includes or is otherwise coupled to a corresponding cable pulley 608*c*, 608*d*, 608*e*, and 608*f*, and each cable pulley 608*c-f* is configured to be operatively coupled to (e.g., has wrapped there around, at least partially) a corresponding one of the drive cables 408*a-d*. In the illustrated embodiment, the first drive cable 408*a* terminates at cable pulley 608*d* ultimately driven by actuation of the fourth capstan assembly 602*d*, the second drive cable 408*b* terminates at cable pulley 608*f* ultimately driven by actuation of the sixth capstan assembly 602*f*, the third drive cable 408*c* terminates at cable pulley 608*c* ultimately driven by actuation of the third capstan assembly 602*c*, and the fourth drive cable 408*d* terminates at cable pulley 608*e* ultimately driven by actuation of the fifth capstan assembly 602*e*.

Accordingly, actuation of the fourth capstan assembly 602*d* (via operation of the third drive input 506*c* of FIG. 5) will correspondingly control movement of the first drive cable 408*a*; actuation of the sixth capstan assembly 602*f* (via operation of the fifth drive input 506*e* of FIG. 5) will correspondingly control movement of the second drive cable 408*b*; actuation of the third capstan assembly 602*c* (via operation of the second drive input 506*b* of FIG. 5) will correspondingly control movement of the third drive cable 408*c*; and actuation of the fifth capstan assembly 602*e* (via operation of the fourth drive input 506*d* of FIG. 5) will correspondingly control movement of the fourth drive cable 408*d*.

Knife Assemblies

Figure 7A:
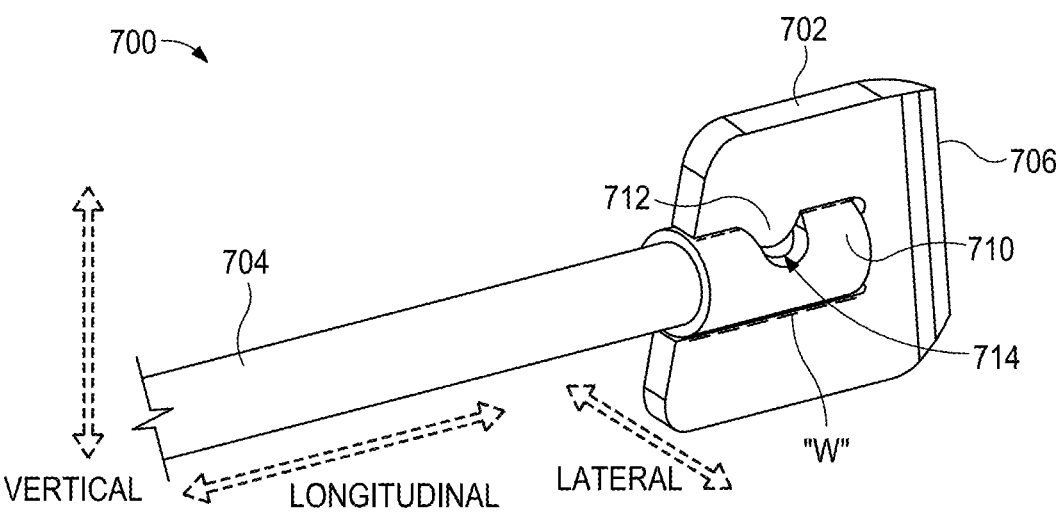
FIGS. 7A and 7B are partial isometric and top views, respectively, of a knife assembly including a blade member secured to a distal portion of a drive rod with an intermediate ferrule.
Figure 7B:
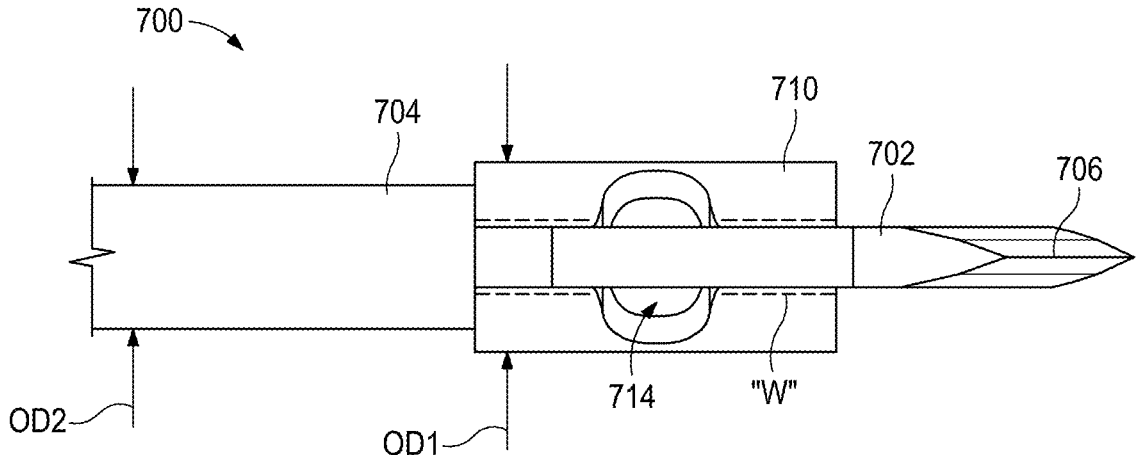

Referring now to FIGS. 7A and 7B, a knife assembly 700 is illustrated and includes a blade member 702 secured to a distal portion (end) of a drive rod 704. The blade member 702 may serve as, or take the place of, the blade member 420 (FIG. 4B) described above and the drive rod 704 may serve as, or take the place of, the drive rod 416 (FIG. 4B and FIG. 6) described above. Similarly, each blade member described hereinafter may serve as the blade member 420 and each drive rod described hereinafter may serve as the drive rod 416. The drive rod 704 defines and otherwise extends in a "longitudinal" direction. A "vertical" direction and a "lateral" or horizontal direction are defined orthogonally to the longitudinal direction as indicated by the arrows illustrated in FIG. 7A. The longitudinal, vertical and lateral directions are used in reference to each of the knife assemblies described hereinbelow.

The blade member 702 may be fabricated from a first material, for example, 420 or 440 stainless-steel with a tissue cutting edge 706 formed at a distal end thereof. The blade member 702 may be distally extended through the guide track 422 (FIG. 4B) to sever tissue with the cutting edge 706. To extend the blade member 702, the drive rod 704 may be translated with the longitudinally driven gear 606*b* (FIG. 6) by rotating the drive gear 604*b* (FIG. 6) with the drive input 506*f*, as described above. Since the drive rod 704 extends through the wrist 206 (FIG. 2) to operably couple the blade member 702 with the gear 606*b* (FIG. 6), at least a distal portion of the drive rod 704 may be constructed of a flexible material to permit the wrist 206 to articulate the end effector 204 with respect to the shaft 202 (FIG. 2). For example, the distal portion of the drive rod 704 may be constructed from a second material, which may include a variety of materials including, but not limited to, a metal (e.g., titanium, tungsten, nitinol, stainless-steel, etc.), a polymer (e.g., ultra-high molecular weight polyethylene), a composite material (e.g., carbon fiber), or any combination thereof. In some embodiments, the first material and the second material are dissimilar from one another, and in other embodiments, the first material and the second material are similar to one another. Where the blade member 702 and the distal portion of the drive rod 704 are constructed of dissimilar materials, it may be difficult to join the blade member 702 to the drive rod 704 with conventional attachment mechanisms, such as welding. Accordingly, the knife assembly 700 includes an intermediate ferrule 710 connecting the blade member 702 and the drive rod 704.

In some embodiments, the ferrule 710 may be constructed as a hollow, stainless-steel cylinder, which may be swaged to the distal portion (end) of the drive rod 704. For example, the ferrule 710 may be positioned (received) on the distal end of the drive rod 704, and subsequently deformed by a press, a hammer, etc. to mechanically grip the drive rod 704. The blade member 702 may then be installed laterally over the ferrule 710. In some applications, the blade member 702 may include a projection 712 that interfaces with a corresponding channel 714 extending laterally across the ferrule 710 to ensure a proper position of the blade member 702. Since the ferrule 710 may be constructed of a similar stainless-steel material as the blade member 702, the blade member 702 may be readily welded to the ferrule 710. For example, welds may be established at weld interfaces "W" to complete the knife assembly 700.

The ferrule 710 may facilitate the connection of the blade member 702 to the drive rod 704 when first material of the blade member 702 and second material of the drive rod 704 are dissimilar materials, but the ferrule 710 does have a larger outer diameter OD1 than an outer diameter OD2 of the drive rod 704. The increased dimension (diameter) of the ferrule 710 may complicate the construction or design of the guide track 422 or jaw 212 (FIG. 4B). Thus, in some embodiments, it may be helpful to directly couple a blade member to the distal portion of a drive rod.

Referring now to FIGS. 8A through 8C, a knife assembly 800 is illustrated in which a blade member 802 is coupled directly to a drive rod 804 by a thermal spray. The blade member 802 may be constructed of the first material and the drive rod 804 may be constructed of the second material that is dissimilar from the first material. The blade member 802 includes a cutting edge 806 at a distal or leading end thereof. In the illustrated embodiment, the cutting edge 806 tapers inwardly in a proximal direction from both an upper edge 806U and a lower edge 806L of the cutting edge 806, and thereby defines a V-shape having a vertex along a central axis "X0" of the knife assembly 800. In other embodiments, the cutting edge 806 may be straight, orthogonal to the central axis "X0," tapered along a single inclination angle with respect to the central axis "X0", or otherwise arranged without departing from the scope of the disclosure.

The blade member 802 includes or otherwise defines a slot 808 extending along the central axis "X0" for receiving a distal end or portion 804D of the drive rod 804. In the illustrated embodiment, the distal portion 804D of the drive rod 804 is similar in cross section to a proximal portion 804P of the drive rod 804. In particular, the distal and proximal portions 804D, 804P are both cylindrical. In other embodiments, (see, e.g., FIGS. 12A, 13A and 14C), the distal and proximal portions of a drive rod may be dissimilar in cross section. The slot 808 may have (exhibit) a width "W" that is the same nominal size as the outer diameter OD2 of the drive rod 804. In some embodiments, the distal portion 804D may be ground and otherwise machined to closely fit within the slot 808, with a predetermined tolerance from the outer diameter OD2 of the drive rod 804, for example, about #0.02 mm (+0.001 inches). Once the distal portion 804D is received within the slot 808, the blade member 802 may be affixed to the drive rod 804 by applying a thermal spray to an interface or intersection "I" defined between the blade member 802 and the distal portion 804D of the drive rod 804.

A thermal spray is an industrial coating process that heats or melts a metallic, plastic, composite or ceramic feedstock, and deposits the material on to a surface in a molten or semi-molten form by spraying micrometer-sized particles onto the surface within a carrier gas. An accumulation of the particles results in a coating without significantly heating the surface. Thus, where the thermal spray forms a coating over a surface formed of dissimilar materials such as the first and second materials of the blade member 802 and the distal portion 804D of the drive rod, the dissimilar materials may be effectively joined without impairing axial strength or a bending fatigue life of the knife assembly 800.

As shown in the enlarged view of FIG. 8C, a coating 810 may be formed (applied) at the intersection "I". The coating 810 may be formed from aluminum, copper, magnesium, titanium, steel or other materials, and may be deposited to a depth in a range from about from a few microns to several millimeters. In some embodiments, the coating 810 may have a depth of about 0.08 inches or more. In some embodiments, the coating 810 may be ground such that an outer diameter OD3 of the coating 810 matches the outer diameter OD2 of the drive rod 804. In other embodiments (not shown), the coating 810 may protrude radially outward from the drive rod 804. The coating 810 may engage the jaw 212 (FIG. 4B) as the blade member 802 traverses the guide track 422 to constrain the blade member 802 from any unintended twisting or other unintended movement.

In some other embodiments, the distal portion 804D of the drive rod 804 may be formed with a reduced outer diameter OD4 with respect to the outer diameter OD2 of the proximal portion 804P of the drive rod 804. The reduced outer diameter OD2 may be smaller than the width "W" of the slot 808 (FIG. 8A), and the thermal spray coating 810 may be applied to the distal portion 804D until the coating 810 exhibits the outer diameter OD3, which may be substantially similar to the width "W" of the slot 808. The coated distal portion 804D may then be inserted into the slot 808 of the blade member 802, and the thermal spray coating 810 may be readily welded to the blade member 802. For example, a laser weld formed at the intersection "I" of the coating 810 and the blade member 802 may join the drive rod 802 to the blade member 802.

Figure 9A:
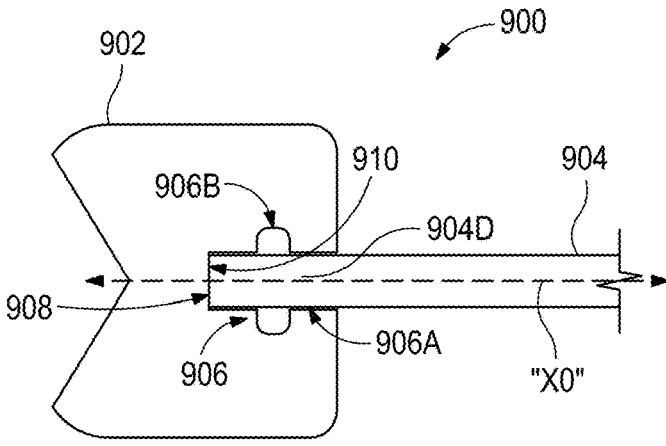
FIGS. 9A, 9B and 9C are side views of alternate knife assemblies illustrating various configurations for the distal portion of a drive rod and a slot formed in a blade member to receive the distal portion of the drive rod in accordance with one or more embodiments consistent with the present disclosure.
Figure 9B:
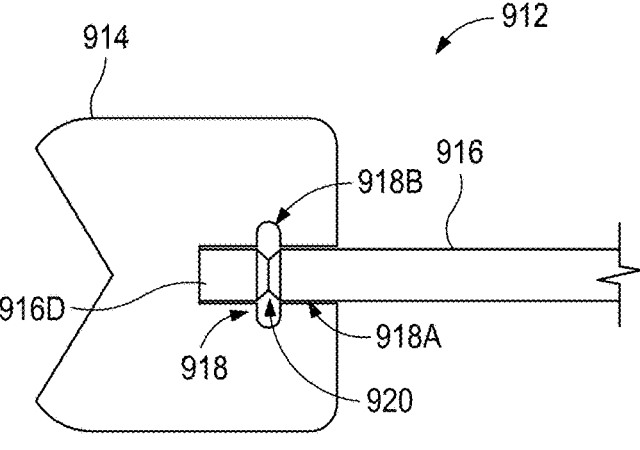
Figure 9C:
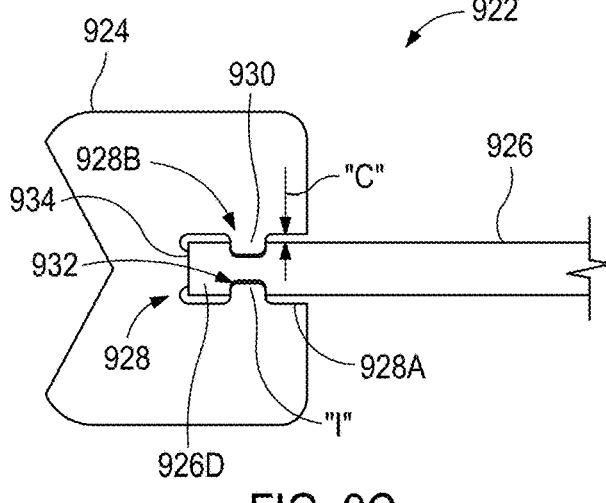

FIGS. 9A through 9C illustrate various configurations for the distal portion of a drive rod and a slot formed in a blade member, which may facilitate directly joining the drive rod and blade member together with a thermal spray.

FIG. 9A illustrates a knife assembly 900 including a blade member 902 and a drive rod 904 having a distal end or "portion" 904D. The blade member 902 includes and otherwise defines a slot 906 therein, which includes a longitudinal portion 906A extending along the central axis "X0", and a plurality of vertical extensions 906B extend vertically (radially or laterally outward) from the longitudinal portion 906A. The vertical extensions 906B comprise voids (apertures) in the blade member 902 and extend from the longitudinal portion 906A of the slot 906. The longitudinal portion 906A may be sized to closely receive the distal portion 904D of the drive rod 904 therein. In the illustrated embodiment, two vertical extensions 906B are aligned with one another extending outward on opposite sides of the longitudinal portion 906A. In other embodiments, more or fewer vertical extensions 906B may be provided in aligned or unaligned configurations.

The drive rod 904 includes a flat distal face 908 that may abut a distal face 910 of the longitudinal portion 906A of the slot 906. In other embodiments, the drive rod 904 may be rounded or curved at the distal end, similar to the drive rod 804 described above. The vertical extensions 906B may allow a thermal spray to accumulate therein, and a coating to be formed on lateral surfaces of the blade member 904 within the slot 906. This arrangement may prove advantageous in providing a strong bond between the blade member 902 and the drive rod 904.

FIG. 9B illustrates a knife assembly 912 including a blade member 914 and a drive rod 916 having a distal portion 916D. The blade member 914 includes or defines a slot 918 with a longitudinal portion 918A, in which the distal portion 916D of the drive rod 916 may be closely received. The slot 918 also includes (defines) vertical extensions 918B, similar in some respects to the blade member 902 described above. In knife assembly 912, however, the distal portion 916D of the drive rod 916 includes a circumferential notch 920 that can be longitudinally aligned with the vertical extensions 918B. The circumferential notch 920 comprises a reduced-diameter portion of the drive rod 916 extending circumferentially around the drive rod 916. In the illustrated embodiment, the circumferential notch 920 exhibits a V-shaped cross section, but in other embodiments, the circumferential notch 920 may be u-shaped, square shaped, semi-circular, etc. without departing from the scope of the disclosure. Longitudinally aligning the circumferential notch 920 with the vertical extensions 918B permits a thermal spray to accumulate on longitudinally facing surfaces of both the blade member 914 and the drive rod 916. A bond between the blade member 914 and the drive rod 916 may thereby be strengthened, permitting greater longitudinal forces to be applied through the drive rod 916 and blade member 914 to tissue grasped in the end effector 204 (FIG. 4A). In other embodiments, the circumferential notch 920 may be provided on the drive rod 916 even when vertical extensions 918B are not provided, e.g., the drive rod 916 may be joined to the blade member 802 (FIG. 8A) that does not include the vertical extensions. The circumferential notch 920 may still increase the bonding strength and retention between the drive rod 916 and the blade member 802.

FIG. 9C illustrates a knife assembly 922 including a blade member 924 and a drive rod 926 defining (providing) a distal portion 926D. The blade member 924 includes or defines a slot 928 with a longitudinal portion 928A, in which the distal portion 926D of the drive rod 926 may be received. The longitudinal portion 928A may be oversized such that a clearance "C" is defined between the drive rod 926 and the longitudinal portion 928A. In such sections, the clearance C is larger than the outer diameter of the drive rod 926.

The slot 928 also defines a reduced width portion 928B where vertical projections 930 of the blade member 924 extend into the slot 928. The drive rod 926 may provide and otherwise define upper and lower longitudinal channels 932, which may closely receive the vertical projections 930 of the drive rod 926. The blade member 924 may also include a longitudinal projection 934 extending into the slot 928 and abutting the distal end of the drive rod 926. The engagement of the vertical projections 930 with the longitudinal channels 932, and the distal portion of the drive rod 926 with the longitudinal projection 934 allow longitudinal forces to be transmitted between the blade member 924 and the drive rod 926. A thermal spray coating applied at the interface or intersection "I" between the blade member 924 and the drive rod 926 may not be unduly stressed in operation.

Figure 10A:
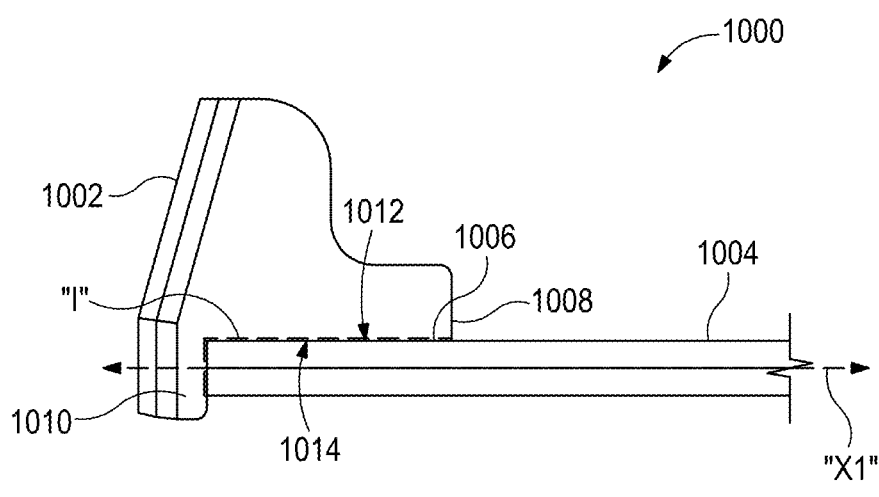
FIGS. 10A, 10B and 10C are side views of alternate knife assemblies illustrating various configurations for the distal portion of a drive rod and a lower edge of a blade member to engage the distal portion of the drive rod in accordance with one or more embodiments consistent with the present disclosure.
Figure 10B:
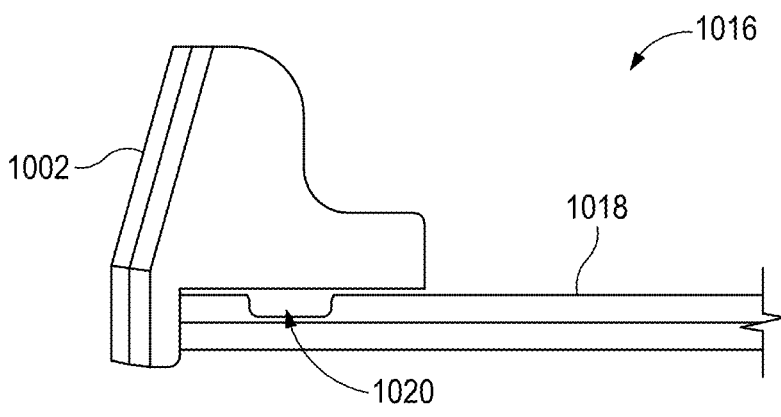
Figure 10C:
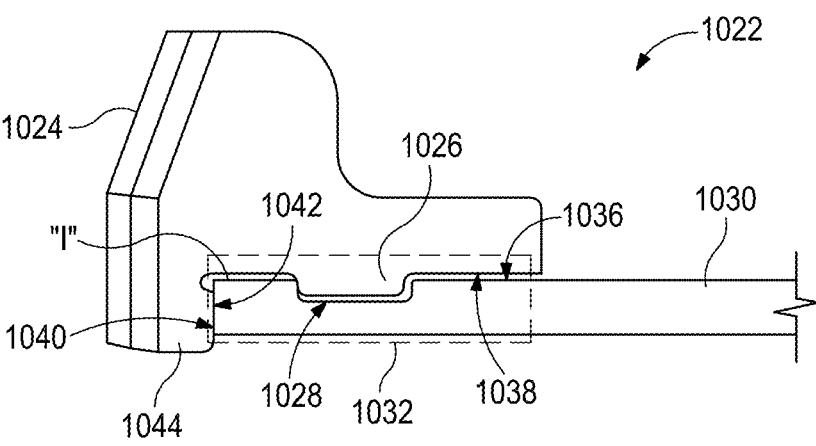

FIGS. 10A, 10B and 10C are side views of alternate knife assemblies where a distal portion of a drive rod engages a lower edge of a blade member, which may facilitate directly joining the drive rod and blade member together with a thermal spray.

FIG. 10A illustrates a knife assembly 1000 including a blade member 1002 and a drive rod 1004. The drive rod 1004 defines a lower (longitudinal) axis "X1" of the knife assembly 1000. The blade member 1002 defines a lower edge 1006 extending longitudinally between a proximal edge 1008 of the blade member 1002 and a distal overhang 1010. The drive rod 1004 abuts (engages) the lower edge 1006 and the distal overhang 1010 of the blade member 1002 to define a generally L-shaped intersection "I" where a thermal spray may be deposited (applied) to couple the blade member 1002 to the driver rod 1004.

In the illustrated embodiment, the drive rod 1004 exhibits a polygonal cross section, e.g., hexagonal, such that a flat upper face 1012 of the drive rod may engage a corresponding flat lower face 1014 of the blade member 1002 at the lower edge 1006. In other embodiments, the drive rod 1004 may be cylindrical (see FIG. 10C) or may have another cross-sectional shape without departing from the scope of the disclosure.

FIG. 10B illustrates a knife assembly 1016 in which the blade member 1002 is coupled to a drive rod 1018 including a lateral channel 1020 defined therein. FIG. 10C illustrates a knife assembly 1022 similar in some respects to the knife assembly 1016 of FIG. 10B. As illustrated, the knife assembly 1022 includes a blade member 1024 defining a vertical projection 1026 that extends into a lateral channel 1028 defined in a drive rod 1030. The lateral channels 1020, 1028 and the vertical projection 1026 may facilitate forming a robust bond with a thermal spray and transmitting longitudinal forces between the blade member 1002, 1024 and drive rod 1018, 1030 as described above.

FIG. 10C also illustrates an additive thermal spray zone 1032 where a thermal spray may be applied to the intersection "I" between the blade member 1024 and the drive rod 1030. The thermal spray zone 1032 is generally rectangular and may be established by masking the areas outside the thermal spray zone 1030. In other embodiments, a thermal spray zone may be established in other non-rectangular shapes and configurations by masking the areas outside the desired thermal spray zone. A thermal spray may thus only accumulate within the thermal spray zone 1032. The additive thermal spray zone 1032 may encompass the entire vertical projection 1026 and lateral channel 1028 as well as portions of an upper face 1036 of the drive rod 1030, a flat lower face 1038 of the blade member 1024, a distal face 1040 of the drive rod 1030 and a proximal face 1042 of an overhang 1044 on the blade member 1024. By depositing a thermal spray onto each of these surfaces of the intersection "I," a robust bond may be generated between the blade member 1024 and the drive rod 1030. Although only one thermal spray zone 1032 is illustrated in FIG. 10C, it will be appreciated that a similar thermal spray zone may be established on an opposite lateral side of the knife assembly 1022 as well.

Figure 11A:
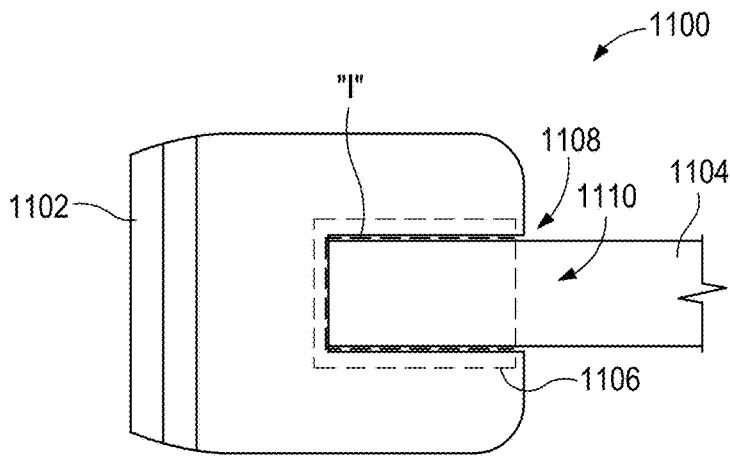
FIGS. 11A, 11B and 11C are side views of alternate knife assemblies illustrating various configurations for an additive thermal spray zone to directly secure the distal portion of a drive rod to a blade member in accordance with one or more embodiments consistent with the present disclosure.
Figure 11B:
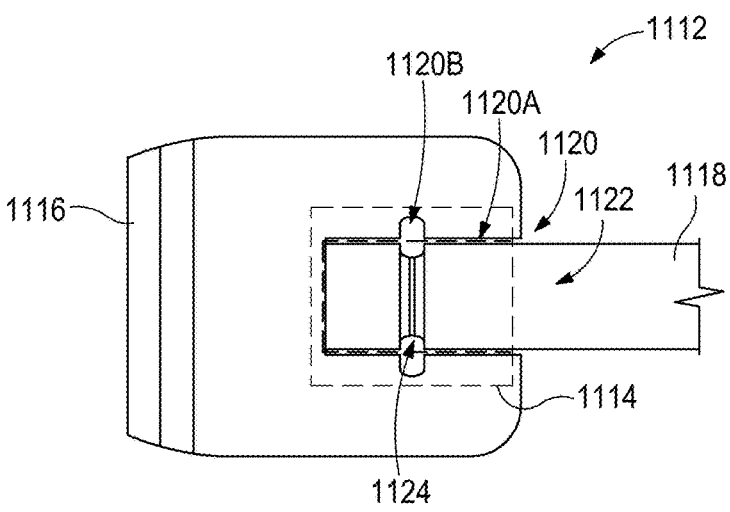
Figure 11C:
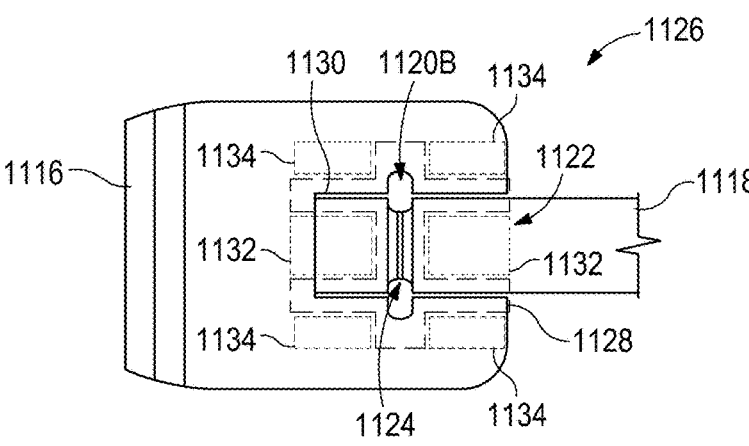

FIGS. 11A through 11C illustrate various configurations for an additive thermal spray zone to directly secure the distal portion of a drive rod to a blade member.

FIG. 11A illustrates a knife assembly 1100 including a blade member 1102 and a drive rod 1104. A thermal spray zone 1106 is depicted and may be generally rectangular and extend vertically across a slot 1108 defined in the blade member 1102 that receives a distal portion 1110 of the drive rod 1104. A thermal spray may thus be deposited across a U-shaped intersection "I" between the distal portion 1110 of the drive rod 1104 and the blade member 1102. Thus, a thermal spray may be deposited over the entire distal portion 1110 of the drive rod 1102.

Similarly, as illustrated in FIG. 11B, a knife assembly 1112 is illustrated with a rectangular thermal spray zone 1114 joining a blade member 1116 and a drive rod 1118. The thermal spray zone 1114 extends vertically across a slot 1120 that includes a longitudinal portion 1120A and one or more vertical extensions 1120B. The thermal spray zone 1114 also encompasses an entire distal portion 1122 of the drive rod 1118, which includes a circumferential notch 1124 longitudinally aligned with the vertical extensions 1120B.

FIG. 11C illustrates a knife assembly 1126 including the blade member 1116 and drive rod 1118 as described above, but with an irregularly shaped thermal spray zone 1128. The thermal spray zone 1128 extends vertically across the vertical extensions 1120B and circumferential notch 1124, and longitudinally along upper and lower edges 1130 of the distal portion 1122 of the drive rod 1118. Vertically medial portions 1132 of the drive rod 1118 and blade member 1116, and corner portions 1134 of the blade member 1116 that are covered by the thermal spray zone 1114 (FIG. 11B), may be excluded from the thermal spray zone 1128. In some embodiments, the portions 1130, 1132 excluded from the thermal spray zone may help control a lateral thickness of the knife assembly, which may facilitate movement of the knife assembly 1126 along the guide track 422 (FIG. 4B).

Figures 12A, 12B:
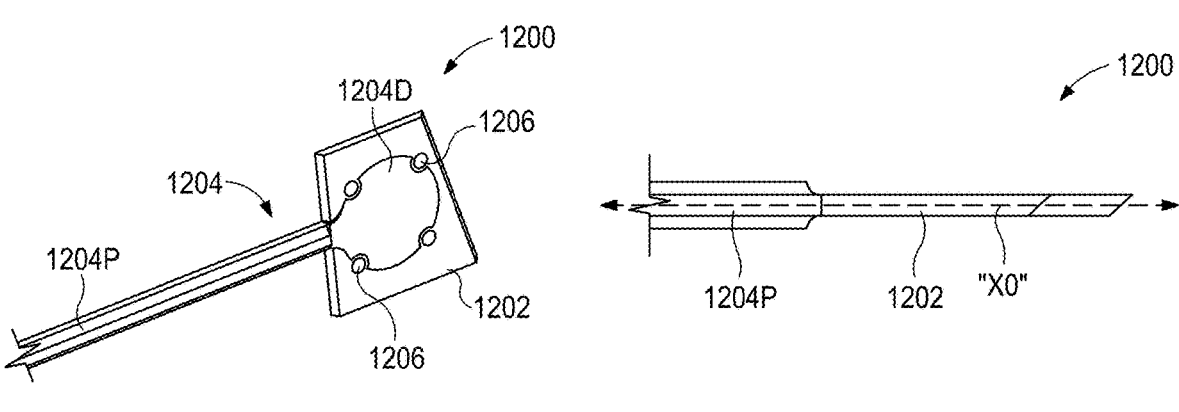
FIGS. 12A and 12B are partial isometric and top views, respectively, of an alternate knife assembly including a paddle at the distal portion of a driver rod swaged directly into a pocket formed in a blade member, consistent with alternate embodiments of the present disclosure.

Referring now to FIGS. 12A and 12B, a knife assembly 1200 is illustrated including a blade member 1202 constructed of a first material (e.g., stainless-steel) coupled directly to a drive rod 1204 constructed of a second material (e.g., nitinol). As illustrated in FIGS. 12A and 12B, the blade member 1202 and the drive rod 1204 may be staked together at four (4) staking locations 1206 spaced around a distal portion 1208 of the drive rod 1204. Generally, staking is a process whereby a boss on one piece is radially expanded with a staking punch to form an interference fit with a hole on a second piece to form a permanent joint between the two pieces. Although the blade member 1202 and the drive rod 1204 are illustrated as being coupled to one another by staking, in alternate embodiments, the blade member 1202 and the drive rod 1204 may additionally or alternatively be joined by a thermal spray process, as described above. Each of the knife assemblies described hereinbelow may be assembled by staking, whether or not the staking locations are explicitly identified, and/or by a thermal spray process.

As illustrated in FIG. 12B, the blade member 1202 is generally aligned with the central axis "X0" defined by a proximal portion 1204P of the drive rod 1204 when the knife assembly 1200 is assembled. In other embodiments, the blade member 1202 may be laterally offset from the central axis "X0" to optimize tensile strength or facilitate construction of the knife assembly 1200.

Figures 12C, 12D:
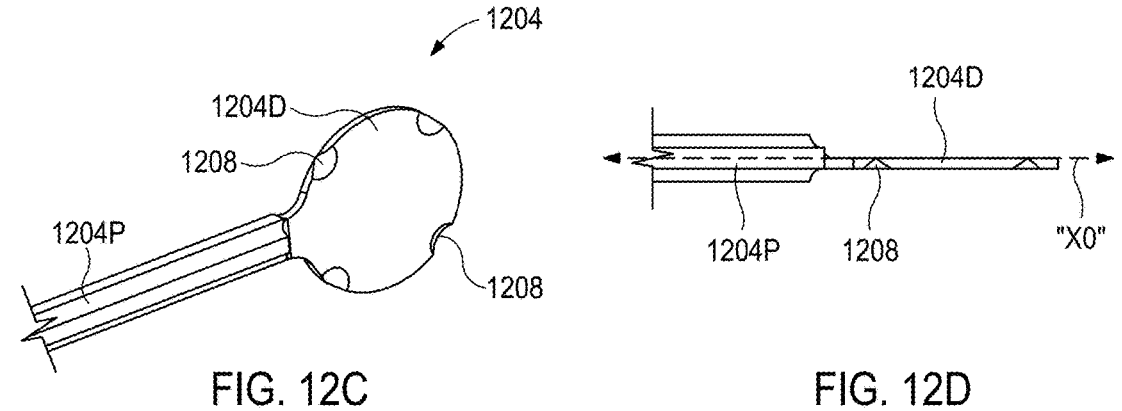
FIGS. 12C and 12D are partial isometric and top views, respectively, of the paddle at the distal portion of the drive rod of FIGS. 12A and 12B.

As illustrated in FIG. 12C, the proximal portion 1204P of the drive rod 1204 may exhibit an octagonal cross section, and the distal portion 1204D may be formed as a circular, flat paddle extending longitudinally and vertically from the proximal portion 1204P. As shown in FIG. 12D, the distal portion 1204D may be laterally offset from the central axis "X0" and may include staking features 1208 (e.g., a boss or hole) formed therein to facilitate assembly with the blade member 1202. In some embodiments, the drive rod 1204 may be constructed of a single piece of flat nitinol material by a photo-chemical machining (PCM) process.

Figure 12E:
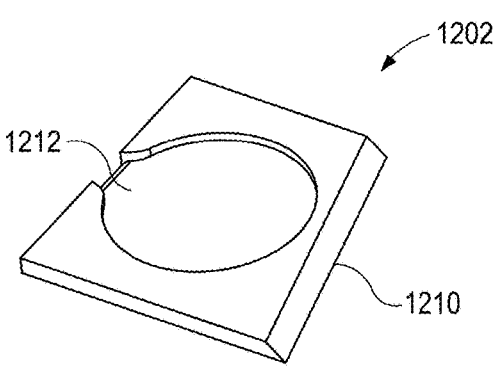
FIG. 12E is an isometric view of the blade member of FIGS. 12A and 12B illustrating the pocket formed therein.

As illustrated in FIG. 12E, the blade member 1202 includes a cutting edge 1210 defined at a distal end and a pocket 1212 defined on a lateral face thereof for receiving the distal portion 1204D of the drive rod 1204. Although not visible in FIG. 12E, staking features may be formed in the pocket 1212 to correspond with the staking features 1208 on the drive rod 1204. The blade member 1202 may be constructed of a single piece of flat stainless-steel material by a PCM process, and then joined to the nitinol drive rod 1204 by staking and/or a thermal spray.

Figure 13A:
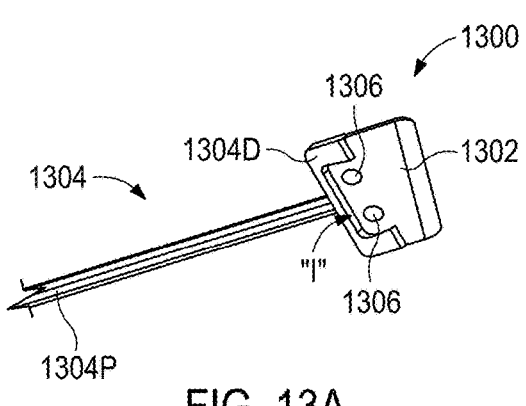
FIGS. 13A and 13B are partial isometric and top views, respectively, of an alternate knife assembly including a pocket formed at the distal portion of a drive rod in which a proximal projection of a blade member is received, consistent with alternate embodiments of the present disclosure.
Figure 13B:
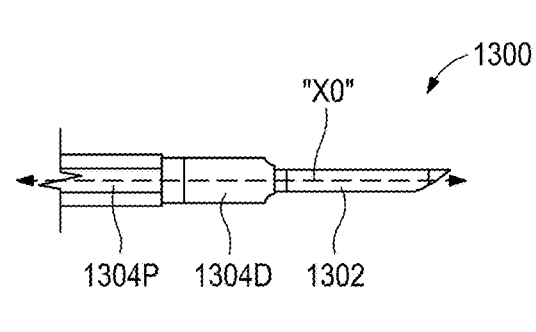

Referring now to FIGS. 13A and 13B, a knife assembly 1300 is illustrated including a blade member 1302 coupled directly to a drive rod 1304. The blade member 1302 may be constructed of a first material such as stainless-steel and the drive rod 1304 may be constructed of a second material different from the first material, such as nitinol. In some embodiments, a permanent joint may be established between the dissimilar materials by staking the blade member 1302 to the drive rod 1304 at staking locations 1306. In other embodiments, a thermal spray may be applied to at least a portion of the intersection "I" between the blade member 1302 and the drive rod 1304 to permanently join the two components to one another.

As illustrated in FIG. 13B, the blade member 1302 may be vertically arranged and generally aligned with the central axis "X0" defined by an elongated proximal portion 1304P of the drive rod 1204 when the blade member 1302 is joined to a distal portion 1304D of the drive rod 1304.

Figure 13C:
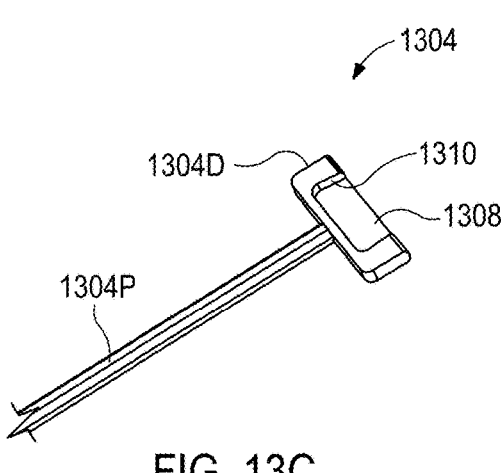
FIGS. 13C and 13D are partial isometric and top views, respectively, of the pocket formed at the distal portion of the drive rod of FIGS. 15A and 15B.
Figure 13D:
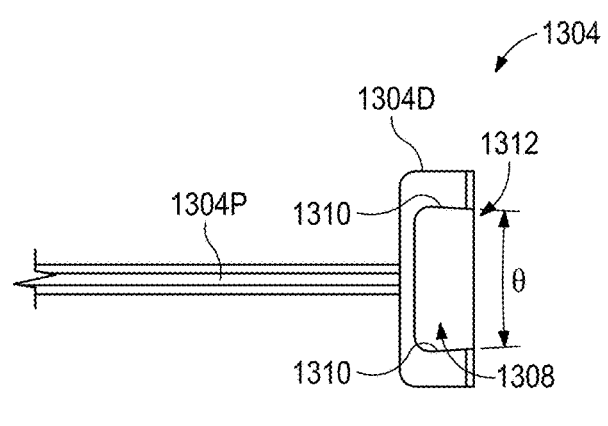

As illustrated in FIGS. 13C and 13D, the distal portion 1304D of the drive rod 1304 protrudes vertically (laterally outward) from the proximal portion 1304P and includes a pocket 1308 defined therein for receiving the blade member 1302. A depth of the pocket 1308 may be controlled or optimized to define a lateral position of the blade member 1302 with respect to the central axis "X0" of the knife assembly 1300. The pocket 1308 includes upper and lower walls 1310, which may be tapered inwardly toward a distal opening 1312. As illustrated in FIG. 13D, the upper and lower walls 1310 are tapered at an angle θ of about 10 degrees from the central axis "X0" and/or one another. In other embodiments, the angle θ may be higher or lower without departing from the scope of the disclosure.

Figure 13E:
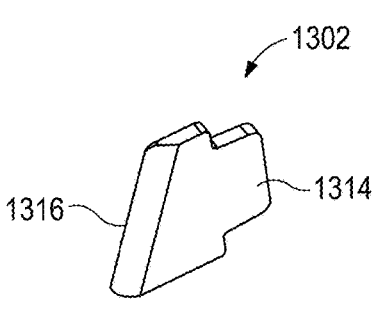
FIGS. 13E and 13F are isometric and side views, respectively, of the blade member of FIGS. 15A and 15B illustrating the proximal projection formed thereon.
Figure 13F:
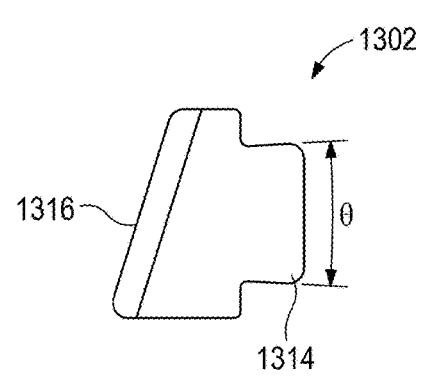

As shown in FIGS. 13E and 13F, the blade member 1302 may include a tail portion 1314 opposite a cutting edge 1316. The tail portion 1314 may be tapered outwardly at the angle θ, such that the tail portion 1314 may be received within the pocket 1308 to permit longitudinal forces to be transmitted through drive rod 1304 to the blade member 1302.

Figures 14A, 14B:
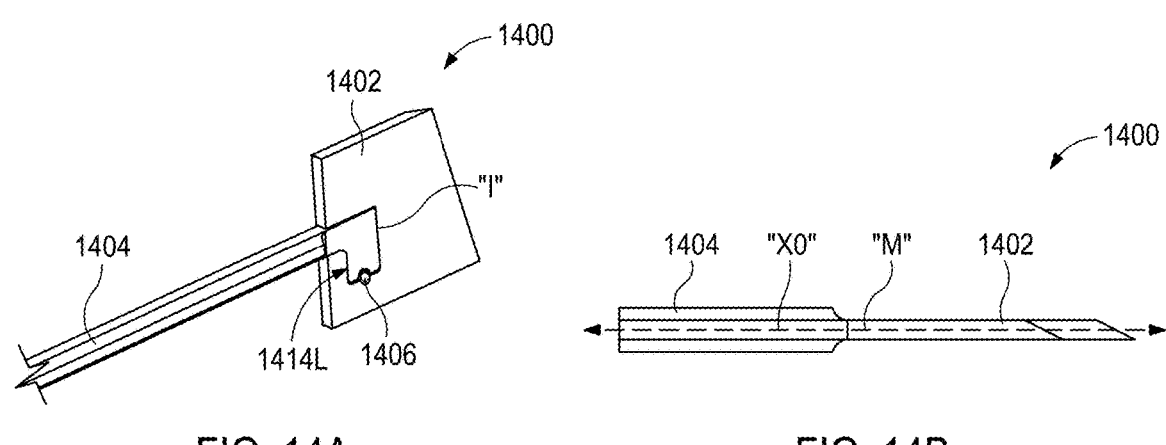
FIGS. 14A and 14B are partial isometric and top views, respectively, of an alternate knife assembly including a pair of offset paddles at the distal portion of a drive rod interlocked directly into a corresponding pocket formed in a blade member, consistent with alternate embodiments of the present disclosure.

Referring now to FIGS. 14A and 14B, a knife assembly 1400 is illustrated including a blade member 1402 coupled directly to a drive rod 1404. As in each of the knife assemblies described herein, the blade member 1402 may be constructed of a first material such as stainless-steel and the drive rod 1404 may be constructed of a second material similar or different from the first material, such as stainless-steel or nitinol. A permanent joint may be established between the similar or dissimilar materials by staking the blade member 1402 to the drive rod 1404 at staking locations 1406 (only one staking location is visible in FIG. 14A). In other embodiments, a thermal spray may be applied to the intersection "I" between the blade member 1402 and the drive rod 1404 to permanently join the two components to one another.

As illustrated in FIG. 14B, the blade member 1402 is generally aligned with a midplane "M" defined by the drive rod 1404. The central axis "X0" lies within the midplane "M."

Figures 14C, 14D:
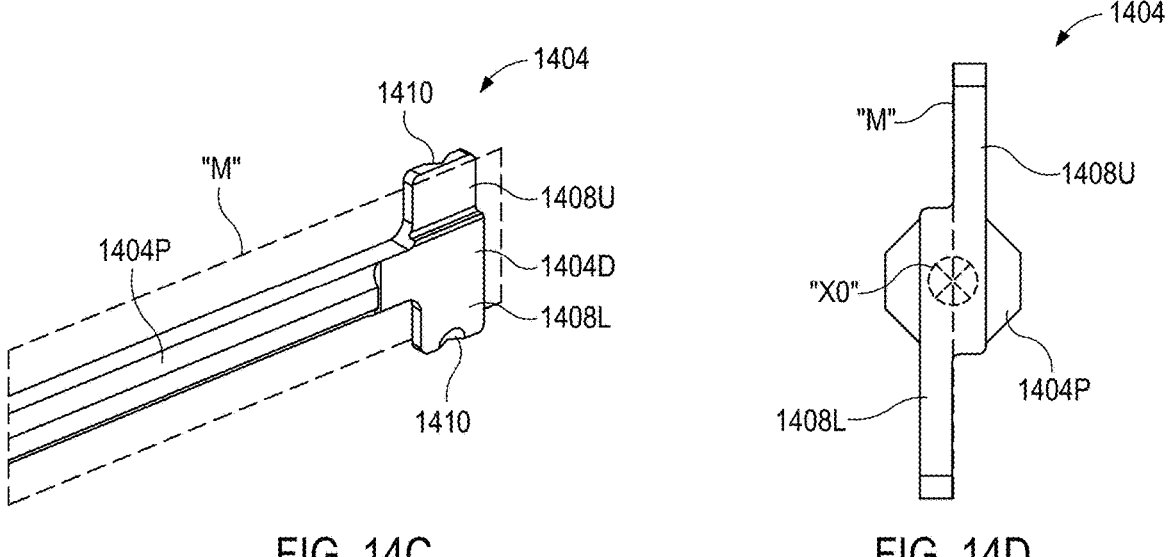
FIGS. 14C and 14D are partial isometric and top views, respectively, of the offset paddles at the distal portion of the drive rod of FIGS. 14A and 14B.

As indicated in FIG. 14C, the drive rod 1404 includes an elongated proximal portion 1404P and exhibits an octagonal cross-section. Round, oval or other polygonal cross-sections are contemplated for the proximal portion 1404P in other embodiments. A distal portion 1404D of the drive rod 1404 includes an upper paddle 1408U and a lower paddle 1408L protruding vertically from the proximal portion 1404P in opposite directions. The upper and lower paddles 1408U, 1408L extend on opposite lateral sides of the medial plane "M." For example, the upper paddle 1408U protrudes upwardly and on a left side of the medial plane "M" from the perspective of a user at a proximal end of the drive rod 1406, and the lower paddle 1408L protrudes downwardly and on a right side of the medial plane "M". The offset upper and lower paddles 1408U, 1408L may be interlocked with the blade member 1402, and coupled thereto using staking features 1410 defined at opposite ends of the paddles 1408U, 1408L.

Figure 14E:
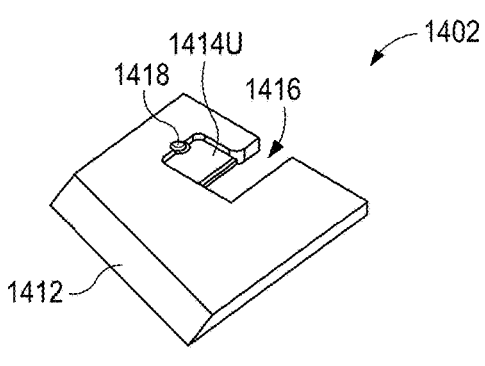
FIG. 14E is an isometric view of the blade member of FIGS. 18A and 18B illustrating the pocket formed therein.

As shown in FIG. 14E, the blade member 1402 includes a cutting edge 1412 defined at a distal end thereof and an upper pocket 1414U defined on a first lateral face thereof as illustrated in FIG. 14E. A lower pocket 1414L (see FIG. 14A) is defined on an opposite lateral face of the blade member 1402, and a central slot 1416 extends laterally through the blade member 1402 between (intersecting) the pockets 1412U, 1412L. Staking features 1418 may be defined at ends of the pockets 1414U, 1414L for engagement with the staking features 1410 defined on the drive rod 1406.

Figure 15A:
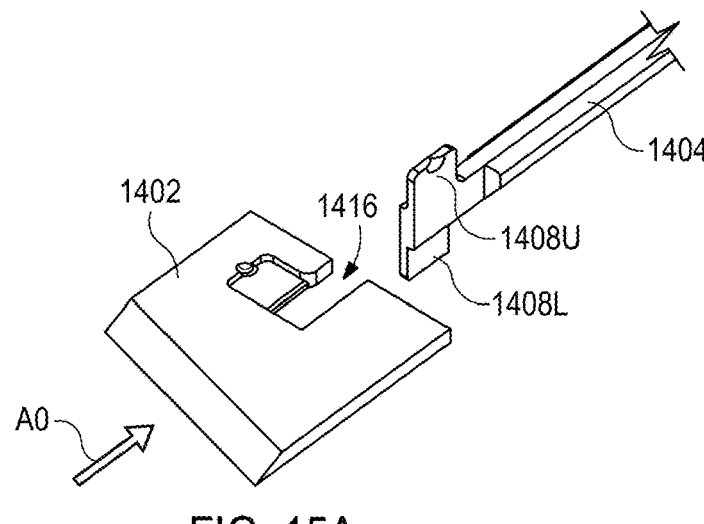
FIGS. 15A, 15B and 15C are partial isometric views of the drive rod and blade member of FIGS. 14A and 14B illustrating a sequence for forming the knife assembly of FIGS. 14A and 14B.
Figure 15B:
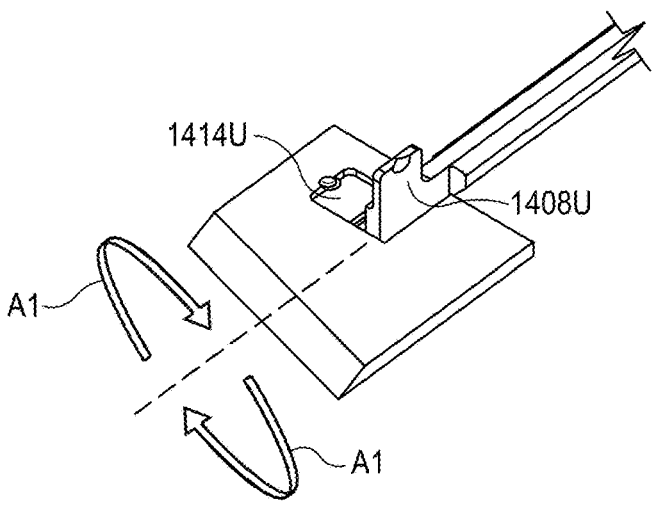
Figure 15C:
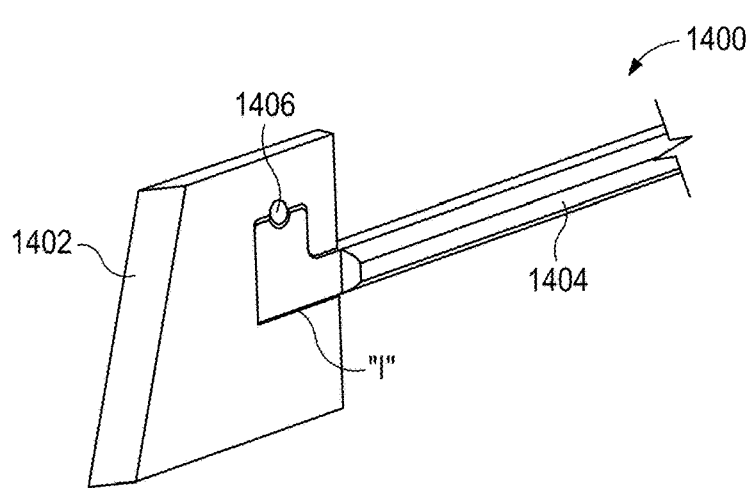

FIGS. 15A, 15B and 15C illustrate progressive steps in forming or assembling the knife assembly 1400 of FIGS. 14A-14E. Initially, as illustrated in FIG. 15A, the blade member 1402 may be approximated with (advanced towards) the drive rod 1404 in the direction arrow $A_0$ until the upper and lower paddles 1408U, 1408L are received into the central slot 1416 of the blade member 1402. The upper and lower paddles 1408U, 1408L may be generally orthogonal to the blade member 1402. Next, as illustrated in FIG. 15B, the blade member 1402 may be rotated in the direction of arrows $A_1$ until the upper and lower paddles 1408U, 1408L are received in the upper and lower pockets 1414U, 1414L (only upper pocket 1414U is visible in FIG. 15B) on opposite sides of the blade member 402. Finally, as illustrated in FIG. 15C, the blade member 1402 and the drive rod 1404 may be staked together at staking locations 1406, and/or coupled together with a thermal spray at the intersection "I' of the blade member 1402 and the drive rod 1406. In this manner, the knife assembly 1400 may be formed. Thereafter, the blade member 1402 may be positioned within an end effector 204 (FIGS. 4A and 4B) of a surgical tool 200 (FIG. 2). A proximal end of the drive rod 1406 may be operably coupled with a drive input 506e (FIG. 5). For example, the drive rod 1406 may be attached to the longitudinally driven gear 606b, which is responsive to rotation of the drive input 506e as described above. Thus, actuation of the drive input 506e will translate the drive rod 1406 longitudinally through the elongated shaft 202 (FIG. 6) and translates the blade member 1402 within the end effector 204.

Figure 16:
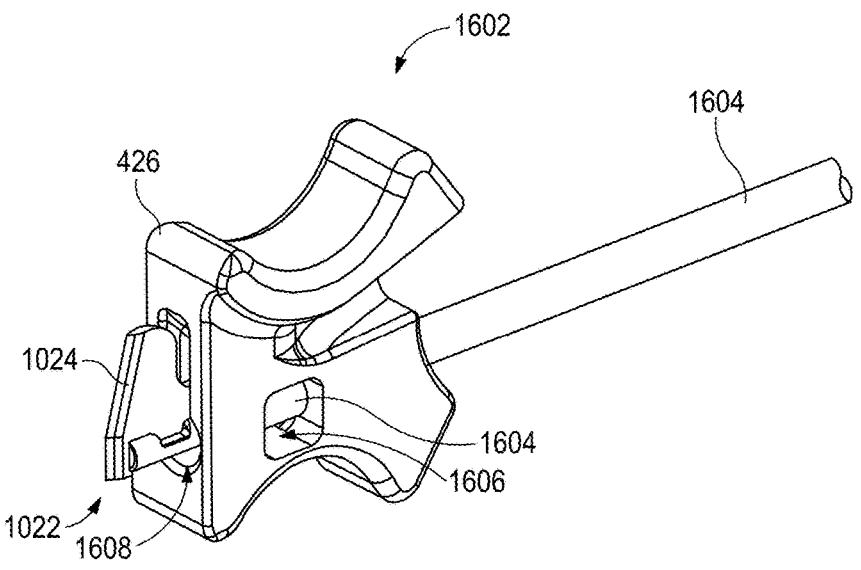
FIG. 16 is a partial perspective view of a knife assembly including a distal support mechanism for the knife assembly of FIG. 10C.

FIG. 16 is a partial perspective view of an example knife assembly 1600 including a distal support mechanism 1602 in accordance with embodiments of the present disclosure. As illustrated, the distal support mechanism 1602 generally provides support for the for the knife assembly 1022 of FIG. 10C. In other embodiments, the distal support mechanism 1602 may provide support for any of the other knife assemblies 700, 800, 900, 912, 922, 1000, 1016, 1100, 1112, 1126, 1200, 1300, 1400 described herein without departing from the scope of the disclosure.

The distal support mechanism 1602 generally includes the distal wedge 426 and a support lumen 1604 extending proximally therefrom. The support lumen 1604 may extend longitudinally through a window 1606, which extends laterally into or through the distal wedge 426. The drive rod 1030 extends through the support lumen 1604 and may be operably coupled to the drive housing 208 (FIG. 2). As indicated above, the distal wedge 426 receives the blade member 420 therein when the blade member is in the "zero" or "home" position. Upon actuation of the second capstan assembly 602b (FIG. 6), via actuation of the sixth drive input 506f (FIG. 5), drive rod 1030 may be advanced through the support lumen 1604 to advance the blade member 420 distally into the guide track 422 (FIG. 4B) through a distal opening 1608 defined in the distal wedge 426. Together, the distal wedge 426 and the support lumen 1604 provide stability and support to the knife assembly 1022 as the blade member 420 is advanced and retracted.

The distal wedge 426 may be constructed of a third material, such as a hard plastic, a metallic material (e.g., stainless steel), or other generally rigid materials. In some embodiments, the distal wedge 426 may be disposed distal to the wrist 206 (FIG. 2) and may remain relatively rigid during operation. The support lumen 1604, however, may extend through the wrist 206, and may be constructed of a flexible material member to permit the wrist 206 to articulate during operation. The flexible material of the support lumen 1604 may include any of the "second materials" mentioned above including, e.g., titanium, tungsten, nitinol, ultra-high molecular weight polyethylene, carbon fiber or other flexible materials recognized in the art.

Figure 17:
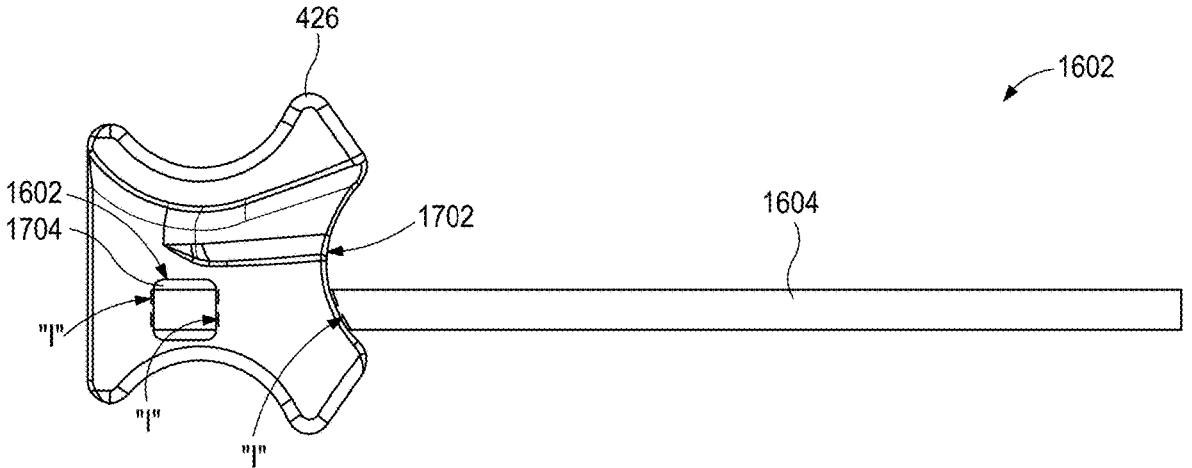
FIG. 17 is a side view of the distal support mechanism of FIG. 16 illustrating a direct connection between a distal wedge and a support lumen in accordance embodiments of the present disclosure.

FIG. 17 is a side view of the distal support mechanism 1602. The distal wedge 426 and the support lumen 1604 may be coupled directly to one another in accordance with at least one embodiment of the present disclosure. An interface or intersection "I" may be defined at the window 1606 and at a proximal face 1702 of the distal wedge 426. A thermal spray coating 1704 may be deposited onto at least a portion of the intersection "I" and, in some embodiments, may substantially fill the window 1606. In other embodiments, the support lumen 1604 may include a circumferential notch (see FIG. 9B) or other geometries within the window 1606, which may strengthen a bond formed by the thermal spray between the distal wedge 426 and the support lumen 1604.

Embodiments disclosed herein include:

A. A surgical tool that includes a drive housing having a drive input rotatably mounted thereon, a shaft extending distally from the drive housing and terminating at an end effector and a knife assembly. The knife assembly includes a blade member arranged at the end effector and movable relative thereto. The blade member is made of a first material and defines a cutting edge at a distal end thereof. The knife assembly further includes a drive rod extending from the drive housing and through the shaft. The drive rod is operably coupled to the drive input such that actuation of the drive input translates the drive rod longitudinally within the shaft, wherein the drive rod includes a distal portion made of a second material dissimilar to the first material, the distal portion of the drive rod being coupled directly to the blade member.

B. A method of constructing a surgical tool including engaging a blade member constructed of a first material with a distal portion of a drive rod constructed of a second material dissimilar to the first material, directly joining the blade member to the distal portion of the drive rod, positioning the blade member within an end effector of the surgical tool and operably coupling a proximal end of the drive rod with a drive input on a drive housing coupled to the end effector by an elongated shaft such that actuation of the drive input translates the drive rod longitudinally through the elongated shaft and translates the blade member within the end effector.

C. A knife assembly for a surgical tool that includes a blade member defining a cutting edge at a distal end thereof and constructed of a first material and a drive rod having a distal portion constructed of a second material, wherein the distal portion of the drive rod is coupled directly to the blade member by at least one of swaging and a thermal spray coating deposited onto at least a portion of an intersection defined between the blade member and the distal portion of the drive rod.

Each of the embodiments A, B and C may have one or more of the following additional elements in any combination: Element 1: wherein the first material is a stainless-steel material, and the second material is a nitinol material. Element 2: wherein the distal portion of the drive rod is coupled directly to the blade member by a thermal spray coating covering at least a portion of an intersection between the distal portion of the drive rod and the blade member. Element 3: wherein the distal portion of the drive rod is swaged directly to the blade member. Element 4: wherein the blade member includes at least one pocket defined in at least one lateral face thereof, and wherein the distal portion of the drive rod includes at least one paddle protruding vertically from an elongated proximal portion of the drive rod, the at least one paddle being received within the at least one pocket. Element 5: wherein the at least one paddle is laterally offset from a central axis defined by the elongated proximal portion of the drive rod. Element 6: wherein the at least one paddle includes an upper paddle protruding upwardly from the elongated proximal portion of the drive rod and a lower paddle protruding downwardly from the elongated proximal portion, the upper and lower paddles being laterally offset from the central axis in opposite directions, the at least one pocket includes an upper pocket and a lower pocket defined on opposite lateral faces of the at least one lateral face and the upper paddle is received in the upper pocket and the lower paddle is received in the lower pocket. Element 7: wherein the elongated proximal portion of the drive rod has a polygonal cross-section. Element 8: wherein the distal portion of the drive rod includes a lateral channel extending therethrough. Element 9: wherein the blade member includes at least one of a vertical projection extending into the lateral channel and a slot having a vertical extension longitudinally aligned with the lateral channel.

Element 10: wherein directly joining the blade member to the distal portion of the dive rod includes depositing a thermal spray onto at least a portion of an intersection defined between the blade member and the distal portion of the drive rod. Element 11: further comprising establishing a thermal spray zone extending across the at least a portion of the intersection by masking portions of the blade member and distal portion of the dive rod outside the thermal spray zone. Element 12: further comprising forming a pocket in a lateral face of the blade member, forming a paddle on the distal portion of the drive rod, the paddle protruding vertically from a proximal portion of the drive rod, and positioning the paddle within in the pocket to define the intersection between the blade member and the distal portion of the drive rod. Element 13: wherein directly joining the blade member to the distal portion of the dive rod swaging the paddle within the pocket. Element 14: further comprising constructing the distal portion of the drive rod of a single piece of flat nitinol material.

Element 15: wherein the first material is dissimilar from the second material and wherein the second material is more flexible than the first material. Element 16: wherein the first material is a stainless-steel material, and the second material is one of nitinol, titanium, tungsten, polyethylene and carbon fiber. Element 17: wherein the intersection is defined between at least one pocket defined in a lateral face of the blade member and a paddle received within the pocket and extending vertically from an elongated proximal portion of the drive rod. Element 18: wherein the elongated proximal portion of the drive rod has an octagonal cross section and is formed along with the distal portion of the drive rod from a single piece of the second material. Element 19: further comprising a distal wedge defining a distal opening these rough which the blade member may be advanced, and a support lumen extending proximally from the distal wedge through which the drive rod extends, wherein the support lumen is constructed of the second material, the distal wedge is constructed of a third material less flexible than the second material, and wherein the thermal spray coating is deposited onto at least an intersection defined between the distal wedge and the support lumen. Element 20: wherein the distal wedge includes a window extending laterally therein, wherein support lumen extends longitudinally through the window, and wherein the thermal spray coating is deposited into the window.

By way of non-limiting example, exemplary combinations applicable to A, B and C include: Element 1 with Element 2; Element 1 with Element 3; Element 4 with Element 5; Element 5 with Element 6; Element 6 with Element 7; Element 8 with Element 9; Element 10 with Element 11; Element 12 with Element 13; Element 13 with Element 14; Element 15 with Element 16; Element 17 with Element 18 and Element 19 with Element 20.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
a drive housing having a drive input rotatably mounted thereon;
a shaft extending distally from the drive housing and terminating at an end effector; and
a knife assembly including:
a blade member arranged at the end effector and movable relative thereto, the blade member being made of a first material and defining a cutting edge at a distal end thereof; and
a drive rod extending from the drive housing and through the shaft, the drive rod being operably coupled to the drive input such that actuation of the drive input translates the drive rod longitudinally within the shaft, wherein the drive rod includes a distal portion made of a second material dissimilar to the first material, the distal portion of the drive rod being coupled directly to the blade member, and
wherein the distal portion of the drive rod is coupled directly to the blade member by a thermal spray coating covering at least a portion of an intersection between the distal portion of the drive rod and the blade member.

2. The surgical tool of claim 1, wherein the first material is a stainless-steel material and the second material is a nitinol material.

3. The surgical tool of claim 1, wherein the blade member includes at least one pocket defined in at least one lateral face thereof, and wherein the distal portion of the drive rod includes at least one paddle protruding vertically from an elongated proximal portion of the drive rod, the at least one paddle being received within the at least one pocket.

4. The surgical tool of claim 3, wherein the at least one paddle is laterally offset from a central axis defined by the elongated proximal portion of the drive rod.

5. The surgical tool of claim 1, wherein the distal portion of the drive rod includes a lateral channel extending therethrough.

6. The surgical tool of claim 5, wherein the blade member includes at least one of a vertical projection extending into the lateral channel and a slot having a vertical extension longitudinally aligned with the lateral channel.

7. A surgical tool, comprising:
a drive housing having a drive input rotatably mounted thereon;
a shaft extending distally from the drive housing and terminating at an end effector; and
a knife assembly including:
a blade member arranged at the end effector and movable relative thereto, the blade member being made of a first material and defining a cutting edge at a distal end thereof; and
a drive rod extending from the drive housing and through the shaft, the drive rod being operably coupled to the drive input such that actuation of the drive input translates the drive rod longitudinally within the shaft, wherein the drive rod includes a distal portion made of a second material dissimilar to the first material, the distal portion of the drive rod being coupled directly to the blade member,
wherein the blade member includes at least one pocket defined in at least one lateral face thereof, and wherein the distal portion of the drive rod includes at least one paddle protruding vertically from an elongated proximal portion of the drive rod, the at least one paddle being received within the at least one pocket,
wherein the at least one paddle is laterally offset from a central axis defined by the elongated proximal portion of the drive rod, and
wherein the at least one paddle includes an upper paddle protruding upwardly from the elongated proximal portion of the drive rod and a lower paddle protruding downwardly from the elongated proximal portion, the upper and lower paddles being laterally offset from the central axis in opposite directions;
the at least one pocket includes an upper pocket and a lower pocket defined on opposite lateral faces of the at least one lateral face; and
the upper paddle is received in the upper pocket and the lower paddle is received in the lower pocket.

8. The surgical tool of claim 7, wherein the elongated proximal portion of the drive rod has a polygonal cross-section.

9. The surgical tool of claim 7, wherein the blade member and the drive rod are staked together at a plurality of staking locations defined at opposite ends of the upper and lower paddles.

10. The surgical tool of claim 7, wherein the blade member includes a central slot extending laterally through the blade member between the upper pocket and the lower pocket.

11. A method of constructing a surgical tool, comprising:
engaging a blade member constructed of a first material with a distal portion of a drive rod constructed of a second material dissimilar to the first material;
directly joining the blade member to the distal portion of the drive rod;
positioning the blade member within an end effector of the surgical tool; and
operably coupling a proximal end of the drive rod with a drive input on a drive housing coupled to the end effector by an elongated shaft such that actuation of the drive input translates the drive rod longitudinally through the elongated shaft and translates the blade member within the end effector, wherein directly joining the blade member to the distal portion of the dive rod includes:

establishing a thermal spray zone extending across at least a portion of an intersection defined between the blade member and the distal portion of the drive rod by masking portions of the blade member and distal portion of the dive rod outside the thermal spray zone; and depositing a thermal spray onto the thermal spray zone.

12. The method of claim 11, further comprising:

forming a pocket in a lateral face of the blade member;

forming a paddle on the distal portion of the drive rod, the paddle protruding vertically from a proximal portion of the drive rod; and positioning the paddle within in the pocket to define the intersection between the blade member and the distal portion of the drive rod.

13. The method of claim 12, wherein directly joining the blade member to the distal portion of the dive rod swaging the paddle within the pocket.

14. A knife assembly for a surgical tool, the knife assembly comprising:

a blade member defining a cutting edge at a distal end thereof and constructed of a first material; and a drive rod having a distal portion constructed of a second material, wherein the distal portion of the drive rod is coupled directly to the blade member by at least one of swaging and a thermal spray coating deposited onto at least a portion of an intersection defined between the blade member and the distal portion of the drive rod.

15. The knife assembly of claim 14, wherein the first material is dissimilar from the second material and wherein the second material is more flexible than the first material.

16. The knife assembly of claim 15, wherein the first material is a stainless-steel material, and the second material is one of nitinol, titanium, tungsten, polyethylene and carbon fiber.

17. The knife assembly of claim 14, wherein the intersection is defined between at least one pocket defined in a lateral face of the blade member and a paddle received within the pocket and extending vertically from an elongated proximal portion of the drive rod.

18. The knife assembly of claim 17, wherein the elongated proximal portion of the drive rod has an octagonal cross section and is formed along with the distal portion of the drive rod from a single piece of the second material.

19. The knife assembly of claim 14, further comprising a distal wedge defining a distal opening these rough which the blade member may be advanced, and a support lumen extending proximally from the distal wedge through which the drive rod extends, wherein the support lumen is constructed of the second material, the distal wedge is constructed of a third material less flexible than the second material, and wherein the thermal spray coating is deposited onto at least an intersection defined between the distal wedge and the support lumen.

20. The knife assembly of claim 19, wherein the distal wedge includes a window extending laterally therein, wherein support lumen extends longitudinally through the window, and wherein the thermal spray coating is deposited into the window.

\* \* \* \* \*